United States Patent [19]

Stevens et al.

[11] Patent Number: 5,256,789
[45] Date of Patent: Oct. 26, 1993

[54] ANTIINFLAMMATORY HYDROXAMIC ACIDS AND N-HYDROXYUREAS

[75] Inventors: Rodney W. Stevens; Takafumi Ikeda, both of Handa; Hiroaki Wakabayashi, Chita; Masami Nakane, Nagoya, all of Japan

[73] Assignee: Pfizer Inc., New York, N.Y.

[21] Appl. No.: 835,934

[22] Filed: Feb. 18, 1992

[51] Int. Cl.$^5$ ............... C07D 25/14; A61K 31/47
[52] U.S. Cl. .................................. 514/311; 546/165
[58] Field of Search .................. 546/165; 514/311

[56] References Cited

FOREIGN PATENT DOCUMENTS 9102694  4/1990  PCT Int'l Appl. .

*Primary Examiner*—David B. Springer
*Attorney, Agent, or Firm*—Peter C. Richardson; Gregg C. Benson; D. Stuart McFarlin

[57] ABSTRACT

Compounds having the structure

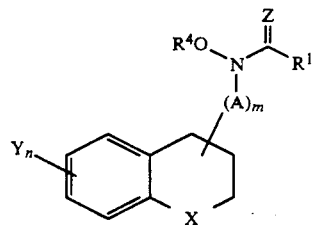

wherein X is nitrogen, oxygen, sulfur or a bond and Z is oxygen or sulfur have been synthesized. These compounds are lipoxygenase inhibitors and are useful as the active agent in pharmaceutical compositions for treating inflammatory conditions in humans and other mammals for which lipoxygenase activity has been implicated.

12 Claims, No Drawings

ANTIINFLAMMATORY HYDROXAMIC ACIDS AND N-HYDROXYUREAS

BACKGROUND OF THE INVENTION

This invention relates to novel hydroxamic acid and N-hydroxyurea derivatives and their use. The compounds of the present invention inhibit the action of lipoxygenase enzyme and are useful in the treatment of inflammatory diseases or conditions in general, for example, allergies and cardiovascular diseases in mammals, including humans. This invention also relates to pharmaceutical compositions comprising such compounds, methods of producing such compounds and methods of using such compounds and compositions in the treatment of the aforementioned diseases and conditions.

Arachidonic acid is known to be the biological precursor of several groups of endogenous metabolites, prostaglandins including prostacyclins, thromboxanes and leukotrienes. The first step of arachidonic acid metabolism is the release of esterified arachidonic acid and related unsaturated fatty acids from membrane phospholipids via the action of phospholipase. Free fatty acids are then metabolized either by cycloxygenase to produce the prostaglandins and thromboxanes or by lipoxygenase to generate hydroperoxy fatty acids which may be further converted to leukotrienes. Leukotrienes have been implicated in the pathophysiology of inflammatory diseases, including rheumatoid arthritis, gout, asthma, ischemia reperfusion injury, psoriasis and inflammatory bowel disease. Any drug that inhibits lipoxygenase is expected to provide significant new therapy for both acute and chronic inflammatory conditions.

Recently, several review articles on lipoxygenase inhibitors have been reported. See, for example, H. Masamune and L. S. Melvin, Sr., in *Annual Reports in Medicinal Chemistry*, 24, 71–80 (Academic Press, 1989) and B. J. Fitzsimmons and J. Rokach in *Leukotrienes and Lipoxygenases*, 424–502 (Elsevier, 1989).

Furthermore, EP 279,263 A2, EP 196,184 A2, JP 63502179 and U.S. Pat. No. 4,822,809 disclose lipoxygenase.

The present inventors have worked to prepare compounds capable of inhibiting the action of lipoxygenase and, after extensive research, have succeeded in synthesizing a series of compounds as disclosed in detail herein.

SUMMARY OF THE INVENTION

The present invention provides for the preparation and use of novel hydroxamic acids and N-hydroxyurea derivatives of the formula:

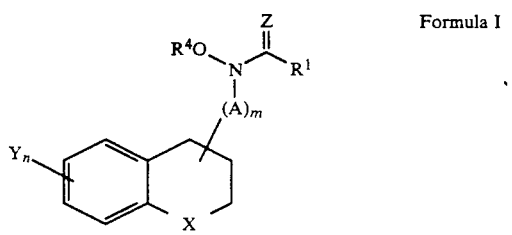

Formula I where $R^1$ is hydrogen, C1 to C4 alkyl, C2 to C4 alkenyl, alkylthioalkyl, alkoxyalkyl or $-NR^2R^3$;

$R^2$ and $R^3$ are each independently hydrogen, C1 to C4 alkyl, hydroxyl, aryl or substituted aryl wherein the substituent or substituents are selected from the group consisting of halo, nitro, cyano, C1 to C12 alkyl, C1 to C12 alkoxy, C1 to C12 hal6substituted alkyl, C1 to C12 hydroxysubstituted alkyl, C1 to C12 alkoxycarbonyl, aminocarbonyl, C1 to C12 alkylaminocarbonyl, C1 to C12 dialkylaminocarbonyl and C1 to C12 alkylsulfonyl, with the proviso that $R^2$ and $R^3$ are not both hydroxyl;

$R^4$ is hydrogen, a pharmaceutically acceptable cation, aroyl or C1 to C12 alkanoyl;

X is a chemical bond, oxygen, sulfur or $NR^5$;

$R^5$ is hydrogen, C1 to C6 alkyl, C3 to C6 alkenyl, C1 to C6 alkanoyl, aryl, arylalkyl or aroyl;

m is 0 or 1;

n is 1 to 3;

A is C1 to C6 alkylene, C2 to C6 alkenylene or C2 to C6 alkylidene;

each Y is independently hydrogen, halogen, hydroxy, cyano, C1 to C12 alkyl, halosubstituted alkyl, hydroxysubstituted alkyl, C2 to C12 alkenyl, C1 to C12 alkoxy, C3 to C12 alkenyloxy, C3 to C8 cycloalkyl, C1 to C8 thioalkyl, C1 to C12 alkoxycarbonyl, C1 to C12 arylalkoxycarbonyl, aminocarbonyl, C1 to C12 alkylaminocarbonyl, C1 to C12 dialkylaminocarbonyl, C1 to C12 arylalkylamino, C1 to C12 arylalkylaminocarbonyl, alkoxyalkyl, aryl, aryloxy, aroyl, C1 to C12 arylalkyl, C2 to C12 arylalkenyl, C1 to C12 arylalkoxy or C1 to C12 arylthioalkoxy wherein said aryl, aryloxy, aroyl, arylalkyl, arylalkenyl, arylalkoxy and arylthioalkoxy may be optionally substituted with a substituent or substituents selected from the group consisting of halo, nitro, cyano, C1 to C12 alkyl, halosubstituted alkyl and. C1 to C12 alkoxy; and Z is oxygen or sulfur.

The substituent(s) Y and the linking group A may be attached at any available position on either ring.

DETAILED DESCRIPTION OF THE INVENTION

As used herein, the term "halo" means fluoro, chloro, brono or iodo.

The term "aryl" as used herein means any substituted and unsubstituted carbocyclic and heterocyclic aromatic groups such as phenyl, naphthyl, pyridyl, furyl and pyrimidinyl. The substituents may be halo, nitro, cyano, C1 to C12 alkyl, C1 to C12 alkoxy, C3 to C12 alkenyloxy, C1 to C12 halosubstituted alkyl, C1 to C12 alkoxycarbonyl, aminocarbonyl, C1 to C12 alkylazinocarbonyl, C1 to C12 halosubstituted alkoxy, C1 to C12 dialkylazinocarbonyl and C1 to C12 alkylsulfonyl.

The term "cycloalkyl" as used herein means a cyclic group of 3 to 8 carbons, such as cyclopropyl, cyclobutyl, cyclopentyl and cyclohexyl.

The term "alkyl" means optionally a straight or branched chain.

The term "aroyl" as used herein means benzoyl, naphthoyl and their derivatives substituted with hydroxy, halo, nitro, cyano, C1 to C12 alkyl, alkoxy, hydroxysubstituted alkyl and halosubstituted alkyl.

The term "pharmaceutically acceptable cation" as used herein means non-toxic cations, including those of alkali and alkaline earth metals such as sodium, lithium, potassium, calcium and magnesium, and organic cations based on ammoniums and amines.

Some of the compounds of Formula I may form acid addition salts. The pharmaceutically acceptable acid addition salts are those formed from acids which form non-toxic acid addition salts, for example, the hydrochloride, hydrobromide, sulfate or bisulfate, phosphate or acid phosphate, acetate, citrate, fumarate, gluconate, lactate, maleate, succinate, tartrate, methanesulfonate, benzenesulfonate, toluenesulfonate and formate salts.

This invention includes pharmaceutical compositions for treatment of inflammatory diseases, allergies and cardiovascular diseases in mammals which comprise a pharmaceutically acceptable carrier or diluent and a compound of Formula I or a pharmaceutically acceptable salt thereof.

This invention also includes pharmaceutical compositions for inhibiting the action of lipoxygenase enzyme in a mammal which comprise a pharmaceutically acceptable carrier and a compound of Formula I or a pharmaceutically acceptable salt thereof.

This invention further includes processes for synthesizing the compounds of Formula I.

This invention still further includes methods of using the novel compounds and compositions in the treatment of conditions and diseases for which lipoxygenase activity has been implicated, for example, inflammatory conditions and diseases.

The compounds of Formula I may be prepared by a number of synthetic methods. In Formulae II, III, IV and V below, Q is

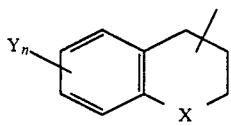

and X, Y, m and n are as defined previously. Although, in reaction Schemes 1 and 2 below, $R^1$ is methyl and $NH_2$, respectively, and Z is oxygen, compounds of Formula I wherein $R^1$ and Z are as defined previously may be prepared in an analogous manner.

In one embodiment, compounds of Formula IV are prepared according to the reaction steps outlined in Scheme 1, below.

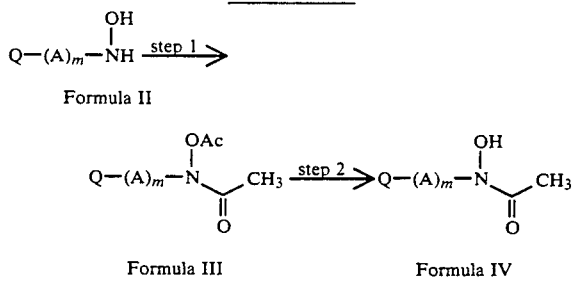

In step 1, the diacetyl compound (III) is prepared by standard methods known in the art. For example, the hydroxylamine (II) is reacted with acetyl chloride or acetic anhydride in a reaction-inert solvent in the presence of a suitable base. Preferred bases are triethylamine and pyridine. Suitable reaction-inert solvents include methylene chloride, chloroform, tetrahydrofuran, benzene and toluene. The reaction is usually carried out in a temperature range of from 0° C. to ambient temperature. Reaction times of from 30 minutes to a few hours are common. The product can be isolated and purified by conventional procedures, for example, recrystallization or chromatography.

Step 2 involves selective hydrolysis of the diacetyl compound (III) with an appropriate base. The bases suitably employed in this reaction include ammonia, ammonium hydroxide, sodium hydroxide, potassium hydroxide and lithium hydroxide, preferably in methanol, ethanol, isopropyl alcohol or water, though binary solvent systems such as alcohol-water, tetrahydrofuran-water and the like may be employed. Reaction temperatures are usually in the range of from −10° C. to ambient temperature and the reaction is usually complete from within a few minutes to several hours. The product, having the structure shown in Formula IV, is isolated by standard methods and purification can be achieved by conventional means, for example recrystallization and chromatography.

In another embodiment, compounds of Formula V are prepared as illustrated in reaction Scheme 2, below.

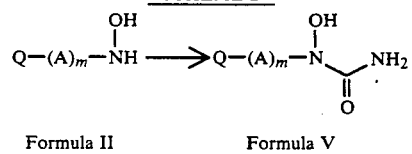

In this step the hydroxylamine (II) is treated with trimethylsilyl isocyanate in a reaction-inert solvent, usually at ambient through to reflux temperature. Suitable solvents which do not react with the reactants and/or products include, for example, tetrahydrofuran, dioxane, methylene chloride and benzene. An alternative procedure employs treatment of the hydroxylamine (II) with gaseous hydrogen chloride in a reaction-inert solvent such as benzene or toluene and then subsequent treatment with phosgene. Reaction temperatures are usually in the range of ambient temperature to the boiling point of the solvent. The intermediate carbamoyl chloride is not isolated but is subjected to (e.g. in situ) reaction with aqueous ammonia. The product thus obtained, having the structure shown in Formula V, is isolated by standard methods and purification can be achieved by conventional means, such as recrystallization and chromatography.

The aforementioned hydroxylamine (II) is easily prepared by standard synthetic procedures from readily available carbonyl compounds, e.g. ketones or aldehydes, or from alcohols or halogen compounds. For example, a suitable carbonyl compound is converted to its oxime and then reduced to the requisite hydroxylamine (II) with a suitable reducing agent (for example, see R. F. Borch, et al., *J. Am. Chem. Soc.*, 93, 2897 (1971)). Preferred reducing agents include sodium cyanoborohydride and borane complexes such as boron-pyridine, boron-triethylamine and boron-dinethylsulfide. Triethylsilane in trifluoroacetic acid may also be employed.

Alternatively, the hydroxylamine (II) can be prepared by treating the corresponding alcohol with N,O-bis(tert-butyloxy-carbonyl)hydroxylamine under Mitsunobu-type reaction conditions followed by acid catalyzed hydrolysis of the N,O-protected intermediate product (See JP 1045344). It is also noteworthy that the N,O-diacetyl compound (III) can be prepared employing N,O-diacetyl hydroxylamine in place of N,O-bis(- tert-butyloxy-carbonyl)hydroxylamine, thus providing a convenient route to the product of Formula IV.

The aforementioned hydroxylamine (II) may also be prepared from a suitable halide compound by reaction with O-protected hydroxylamine and subsequent deprotection (see W. P. Jackson, et al., *J. Med. Chem.*, 31, 499 (1988)). Preferred O-protected hydroxylamines include O-tetrahydropyranyl-, O-trimethylsilyl- and O-benzylhydroxylamine.

The hydroxylamine of Formula II thus obtained by the above representative procedures is isolated by standard methods and purification can be achieved by conventional means, such as recrystallization and chromatography.

The pharmaceutically acceptable salts of the novel compounds of the present invention are readily prepared by contacting said compounds with a stoichiometric amount of an appropriate mineral or organic acid in either-aqueous solution or in a suitable organic solvent. The salt may then be obtained by precipitation or by evaporation of the solvent.

The compounds of this invention inhibit the activity of the lipoxygenase enzyme. This inhibition has been demonstrated by an assay using rat peritoneal cavity resident cells which determines the effect of said compounds on the metabolism of arachidonic acid.

In this test some preferred compounds indicate low $IC_{50}$ values, in the range of 0.1 to 30 $\mu$M, with respect to lipoxygenase inhibition. As used herein, $IC_{50}$ refers to the concentration of the compound tested necessary to effect a 50% inhibition of lipoxygenase.

The ability of the compounds of the present invention to inhibit lipoxygenase enzyme makes them useful for controlling the symptoms induced by the endogenous metabolites arising from arachidonic acid in mammalian subjects. The compounds are therefore valuable in the prevention and treatment of such conditions and disease states in which the accumulation of arachidonic acid metabolites is a causative factor. Examples of such disease states include allergic bronchial asthma, skin disorders, rheumatoid arthritis, osteoarthritis and thrombosis.

Thus, the compounds of Formula I and their pharmaceutically acceptable salts are of particular use in the treatment or alleviation of inflammatory diseases, allergies, cardiovascular diseases in human subjects as well in the inhibition of the lipoxygenase enzyme.

For treatment of the various conditions described above, the compounds of Formula I and their pharmaceutically acceptable salts can be administered to a human subject either alone or, preferably, in combination with pharmaceutically acceptable carriers or diluents in a pharmaceutical composition, according to standard pharmaceutical practice. A compound can be administered by a variety of conventional routes of administration including orally, parenterally and by inhalation. When the compounds are administered orally, the dose range will be generally from about 0.1 to 20 mg/kg body weight of the subject to be treated, per day, preferably from about 0.1 to 1.0 mg/kg/day in single or divided doses. If parenteral administration is desired, then an effective dose will be generally from about 0.1 to 1.0 mg/kg body weight of the subject to be treated, per day. In some instances it may be necessary to use dosages outside these limits, since the dosage will necessarily vary according to the age, weight and response of the individual patient as well as the severity of the patient's symptoms and the potency of the particular compound being administered.

For oral administration, the compounds of Formula I and their pharmaceutically acceptable salts can be administered, for example, in the form of tablets, powders, lozenges, syrups or capsules, or as an aqueous solution or suspension. In the case of tablets for oral use, carriers which are commonly used include lactose and corn starch. In addition, lubricating agents, such as magnesium stearate, are commonly added. In the case of capsules, useful diluents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, sterile injectable solutions of the active ingredient are usually prepared, and the pH of the solutions should be suitably adjusted and buffered. For intravenous use, the total concentration of solute should be controlled to make the preparation isotonic.

The present invention is illustrated by the following examples. However, it should be understood that the invention is not limited to the specific details of these examples. Proton nuclear magnetic resonance spectra (NMR) were measured at 270 MHz unless otherwise indicated, for solutions in perdeuterodimethyl sulfoxide (DMSO-$d_6$) and peak positions are expressed in parts per million (ppm) downfield from tetramethylsilane. The peak shapes are denoted as follows: s, singlet; d, doublet; t, triplet; q, quartet; quint, quintet; m, multiplet; br, broad.

EXAMPLES

EXAMPLE 1

N-(Hydroxy)-N-(indan-1-yl)urea

1-Indanone (4.00 g, 30.3 mmol) and hydroxylamine hydrochloride (5.26 g, 75.7 mmol) were dissolved in a mixture of methanol (40 ml) and pyridine (10 ml) and stirred for 3 hours at ambient temperature. The reaction mixture was concentrated in vacuo and the resultant residue was diluted with 1N HCl (100 ml) and extracted three times with methylene chloride. The organic layer was dried over MgSO$_4$ and concentrated in vacuo to provide 4.13 g (93% yield) of the desired 1-indanone oxime as white needles.

The oxime (4.08 g, 27.7 mmol) prepared in the above step was dissolved in acetic acid (50 ml) and sodium cyanoborohydride (9.40 g, 63 mmol) was added portionwise over 1 hour. After reaction was complete, the reaction mixture was poured carefully into ice cold aqueous Na$_2$CO$_3$ such that the pH was adjusted to 9. The mixture was extracted with methylene chloride, dried over MgSO$_4$ and concentrated in vacuo to afford 3.6 g of 1-indane hydroxylamine (87% yield) as a tan powder.

The hydroxylamine (1.26 g, 8.4 mmol) prepared in the above step was stirred for 1 hour with trimethylsilyl isocyanate (1.65 g, 16.8 mmol) in tetrahydrofuran. The reaction mixture was concentrated in vacuo and the residue recrystallized from ethyl acetate to give 0.78 g (48% yield) of the product as a fine white powder.

m.p.: 158.7°–159.4° C.

IR (KBr): 3465, 3190, 1667, 1654, 1573, 759, 741 cm$^{-1}$,

NMR (CDCl$_3$) δ: 7.34–7.21 (m, 4H), 5.92 (dd, J=5.8 and 8.1 Hz, 1H), 5.3 (br., s, 2H), 5.16 (s, 1H), 3.07–3.02

(m, 1H), 2.95-2.83 (3, 1H), 2.46-2.35 (m, 1H), 2.26-2.13 (m, 1H)

EXAMPLE 2

N-Hydroxy-N-(indan-1-yl)acetamide

1-Indane hydroxylamine (2.33 g, 15.6 mmol), prepared as in Example 1, and triethylamine (3.48 g, 34.3 mmol) were dissolved in methylene chloride (40 ml), cooled to 0° C. and acetyl chloride (2.33 ml, 32.8 mmol) was added. The mixture was stirred for thirty minutes and poured into 1N HCl. The organic layer was separated, dried over $MgSO_4$ and concentrated in vacuo to afford 3.58 g (98% yield) of N-acetoxy-N-(indan-1-yl)acetamide.

The acetamide (3.56 g, 15.3 mmol) was dissolved in a mixture of methanol (20 ml) and ammonia water (10 ml) at ambient temperature. After thirty minutes the mixture was concentrated in vacuo and the residue partitioned between water and methylene chloride. The organic phase was dried over $MgSO_4$ and concentrated in vacuo. The resultant residue was recrystallized from benzene to afford 2.06 g (70% yield) of the product as a fine white powder.

m.p.: 137.9°-139.5° C.

IR (KBr): 3090, 2925, 1615 (br.), 757 $cm^{-1}$,

NMR (DMSO-$d_6$) δ: 9.46 (s, 1H), 7.22-7.12 (m, 4H), 5.96 (br., t, J=8 Hz, 1H), 3.05-2.90 (m, 1H), 2.85-2.70 (m, 1H), 2.25-2.05 (m, 2H), 2.06 (s, 3H)

EXAMPLE 3

N-Hydroxy-N-[2-(2,3-dihydro-1H-inden-1-ylidene)ethyl]acetamide

Diethyl azodicarboxylate (3.94 g) in dry toluene (10 ml) was added to a stirred solution of 2-(2,3-dihydro-1H-idan-1-ylidene) ethanol (2.41 g), N,O-diacetylhydroxylamine (1.85 g) and triphenylphosphine (5.94 g) in dry toluene (60 ml) at $-78°$ C. under nitrogen atmosphere. The mixture was stirred at ambient temperature under nitrogen atmosphere for 30 minutes. The mixture was filtered and the residue was washed thoroughly with ethylacetate and hexane (1:1). The combined filtrate and washings were concentrated under reduced pressure. Chromatography on silica gel eluted with hexane-ethyl acetate (3:1) to give N-acetoxy-N-[2-(2,3-dihydro-1H-inden-1-ylidene) ethyl]acetamide (1.34 g). The diacetate was dissolved in methanol (10 ml), concentrated $NH_4OH$ was added, the mixture was stirred at ambient temperature for 1 hour and concentrated under reduced pressure. The resulting pale yellow oil was extracted with ethyl acetate and washed with brine. The solution was dried over $MgSO_4$ and concentrated to give a pale yellow oil. Chromatography on silica gel eluted with hexane-ethyl acetate (1:1) followed by crystallization from isopropyl ether afforded the desired compound, a white solid (0.46 g).

m.p.: 96.0°-96.6° C.

IR (KBr) v: 1650, 1610,

NMR (270 MHz, $CDCl_3$) δ: 8.30 and 6.40 (br., s, 1H), 7.44-7.51 (m, 1H), 7.16-7.31 (m, 3H), 6.08-6.18 (m, 1H), 4.40 (d, 2H J=6.2 Hz), 3.00-3.09 (m, 2H), 2.78-2.87 (m, 2H), 2.16 (s, 3H).

EXAMPLE 4

N-Hydroxy-N-[1-(1-benzyl-1,2,3,4-tetrahydroquinolin-6-yl)ethyl]urea

To a mixture of 1-benzyl-1,2,3,4-tetrahydroquinolin-6-ylethan-1-ol (2.82 g, 10.6 mmol), BocNH-OBoc (2.48 g, 11.1 mmol) and triphenylphosphine (3.62 g, 13.8 mmol) in toluene (20 ml) was added diethyl azodicarboxylate (2.40 g, 13.8 mmol) at $-78°$ C. under nitrogen atmosphere. The mixture was stirred at $-78°$ to ambient temperature for 30 minutes. The mixture was concentrated in vacuo to give a reddish brown oil (11.87 g). Chromatography on silica gel eluted with hexane-ethyl acetate (15:1) to afford N,O-dibutoxycarbonyl-N-[1-(1-benzyl-1,2,3,4-tetrahydroquinolin-6-yl)ethyl]hydroxylazine (2.57 g, 53.8% yield).

NMR ($CDCl_3$) δ: 7.17-7.35 (a, 5H), 6.91-7.05 (m, 2H, 6.43 (d, J=8.1 Hz, 1H), 5.24 (q, J=6.8 Hz, 1H), 4.45 (s, 2H), 3.34 (t, J=5.5 Hz, 2H), 2.79 (t, J=5.9 Hz, 2H), 1.92-2.05 (m, 2H), 1.21-1.63 (m, 21H).

To a solution of N,O-dibutoxycarbonyl-N-[1-(1-benzyl-1,2,3,4-tetrahydroquinolin-6-yl)ethyl]hydroxylazine (2.57 g, 5.70 mmol) in $CH_2Cl_2$ (30 ml) was added trifluoroacetic acid (9 ml) at ambient temperature. The mixture was stirred at ambient temperature for 1 hour, concentrated in vacuo to afford a viscous oil which was extracted with ethyl acetate and washed with water and brine. The solution was dried over $MgSO_4$ and concentrated to give a yellow oil (1.38 g). Without purification, the crude product was dissolved in tetrahydrofuran (5 ml) and treated with 90% trimethylsilyl isocyanate (1.1 ml, 7.33 mmol) for 1 hour at ambient temperature. Water (1 ml) was added to the mixture which was then concentrated in vacuo. The residue was dissolved in ethyl acetate and the insoluble material was removed by filtration. The filtrate was concentrated in vacuo and crystallized from isopropyl ether-ethyl acetate to give a white solid. Recrystallization from ethyl acetate-isopropyl ether (4:1) afforded the title compound as a white solid (0.223 g, 12% yield).

m.p.: 127.8°-128.2° C. (dec.)

IR (KBr): 3500, 3460, 1645,

NMR (DMSO) δ: 8.84 (s, 1H), 7.18-7.37 (m, 5H), 6.87 (s, 1H), 6.84 (d, J=8.8 Hz, 1H), 6.36 (d, J=8.8 Hz, 1H), 6.15 (s, 2H), 5.11 (q, J=7.0 Hz, 1H), 4.45 (s, 2H), 3.20-3.56* (2H), 2.70 (t, J=6.2 Hz, 2H), 1.80-1.97 (m, 2H), 1.30 (d, J=7.0 Hz, 3H).

* This peak was hidden by $H_2O$ in DMSO-$d_6$.

By analogous methods, the following were prepared.

EXAMPLE 5

N-Hydroxy-N-(indan-2-yl)acetamide

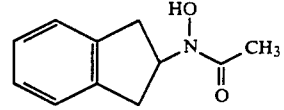

m.p.: 138.8°-140.2° C.

IR: (KBr): 2805, 1580 (br.), 736 $cm^{-1}$.

NMR: ($CDCl_3$) δ: 8.45(br. s, 1H), 7.26-716(m, 4H), 4.85(br., 1H), 3.40 (br., 2H). 3.17-3.08(m, 2H), 2.19(s, 3H).

EXAMPLE 6

N-Hydroxy-N-(indan-2-yl)urea

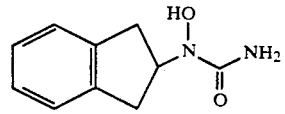

m.p.: 153.4°-154.5° C.

IR: (KBr): 3195, 1627, 740 cm$^{-1}$.

NMR: (DMSO-d$_6$)delta: 9.13 (s, 1H), 7.18-7.08 (m, 4H), 6.37 (br.s, 2H), 5.01 (quint., J=8 Hz), 3.05-2.85 (m, 4H).

EXAMPLE 7

N-Hydroxy-N-(2-phenyl-3,4-dihydro-2H-benzopyran-6-yl)methylacetamide

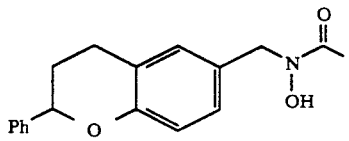

m.p.: 119.5°-121.0° C.

IR: (KBr): 3430, 1611, 1584, 1490.

NMR: (270 MHz, CDCl$_3$) δ 7.26-7.45 (m, 5H), 7.03 (br s, 2H), 6.90 (d, 1H, J=8 Hz), 5.06 (dd, 1H, J=3, 10 Hz), 4.73 (s, 2H), 2.93-3.06 (m, 1H), 2.74-2.86 (m, 1H), 2.03-2.30 (m, 2H), 2.20 (s, 3H).

EXAMPLE 8

N-Hydroxy-N-[2-(indan-1-yl)ethyl]acetamide

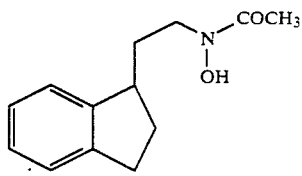

m.p.: oil.

IR: (film, cm$^{-1}$) ν 3160, 1610.

NMR: (270 mHz, CDCl$^3$) δ 8.30-8.55 (br s, 1H), 7.10-7.28 (m, 4H), 3.73 (t, 2H, J=7.3 Hz), 3.13-3.27(m, 1H), 2.79-3.03(m, 2H), 2.25-2.40(m, 2H), 2.10 (s, 3H), 1.90-1.63(m, 2H).

EXAMPLE 9

N-Hydroxy-N-(3,4-dihydro-2H-1-benzopyran-3-yl)acetamide

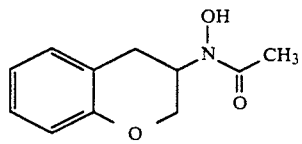

m.p.: 163.6°-163.9° C.

IR: (KBr): 2840, 1618, 1583, 751 cm$^{-1}$.

NMR: (270 MHz, DMSO-d$_6$) δ: 9.78(s, 1H), 7.12-7.04(m, 2H), 6.86(dt, J=1 and 8 Hz, 1H), 6.78(d, J=8 Hz, 1H), 4.68(br. s, 2H), 4.17-4.11(m, 1H), 3.92(t, J=10 Hz, 1H), 3.08(dd, J=11 and 16 Hz, 1H), 2.80(dd, J=4 and 16 Hz, 1H), 2.04(s, 3H).

EXAMPLE 10

N-Hydroxy-N-(5-methoxyindan-1-yl)acetamide

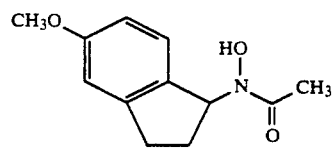

m.p.: 153.5°-154.3° C.

IR: (KBr): 3300, 1604, 1589, 1577 cm$^{-1}$.

NMR: (270 MHz, DMSO-d$_6$) δ: 9.39(s, 1H), 7.01(d, J=8 Hz, 1H), 6.80(d, J=2 Hz, 1H), 6.73(dd, J=2 and 8 Hz, 1H), 5.89(br. s, 1H), 3.72(s, 3H), 3.0-2.89(m, 1H), 2.79-2.73(m, 1H), 2.24-2.0(m, 2H), 2.0(s, 3H).

EXAMPLE 11

N-Hydroxy-N-(5-methoxyindan-1-yl)urea

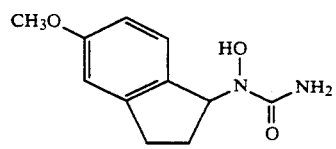

m.p.: 159.3°-159.7° C.

IR: (KBr): 3460, 3200, 1654, 1570 cm$^{-1}$.

NMR: (270 MHz, DMSO-d$_6$) δ: 8.89(s, 1H), 7.05(d, J=8 Hz, 1H), 6.76(d, J=2 Hz, 1H), 6.71(dd, J=2 and 8 Hz, 1H), 6.35 (s, 2H), 5.59(t, J=7 Hz, 1H), 3.71(s, 3H), 2.9-2.86(m, 1H), 2.74-2.71(m, 1H), 2.2-2.0(m, 2H).

EXAMPLE 12

N-Hydroxy-N-(3,4-dihydro-2H-1-benzopyran-3-yl)urea

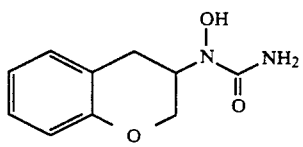

m.p.: 167.9°-168.5° C.

IR: (KBr): 3430, 3145, 1668 cm$^{-1}$.

NMR: (270 MHz, DMSO-d$_6$) δ: 9.30(s, 1H), 7.12-7.04(m, 2H), 6.84(dt, J=1 and 8 Hz, 1H), 6.76(d, J=8 Hz, 1H), 6.49(s, 2H), 4.41-4.37(m, 1H), 4.17-4.11(m, 1H), 3.87(t, J=10 Hz, 1H), 3.05(dd, J=11 and 16 Hz, 1H), 2.68(dd, J=4 and 16 Hz, 1H).

EXAMPLE 13

N-(1-Benzyl-1,2,3,4-tetrahydroquinolin-6-yl)methyl-N-hydroxyacetamide

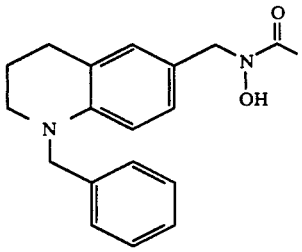

m.p.: 166°-167° C. (dec).

IR: (KBr, cm$^{-1}$) 3125, 2920, 2850, 1604, 1510.

NMR: (270MHz, CDCl$_3$) δ 8.30(br s, 1H), 7.23-7.35(m, 5H), 6.91(br s, 2H), 6.46(d, 1H, J=8Hz), 4.64(s, 2H), 4.47(s, 2H), 3.37(t, 2H, J=6Hz), 2.81(t, 2H, J=6Hz), 2.17(s, 3H), 2.01(quin, 2H, J=6Hz).

EXAMPLE 14

N-Hydroxy-N-(3,4-dihydro-2H-1-benzopyran-2-yl)methylurea

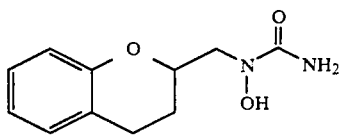

m.p.: 124.4-125.4° C.

IR: (KBr): 3465, 3200, 1633, 1631, 1583, 752 cm$^{-1}$.

NMR: (270 MHz, DMSO-d$_6$) δ: 9.47(s, 1H), 7.04(t, J=8 Hz, 2H), 6.78(dd, J=1 and 8 Hz, 1H), 6.72(d, J=8 Hz, 1H), 6.34(br. s, 2H), 4.22(m, 1H), 3.64(dd, J=6 and 14 Hz, 1H).

EXAMPLE 15

N-Hydroxy-N-(3,4-dihydro-2H-1-benzopyran-2-yl)methylacetamide

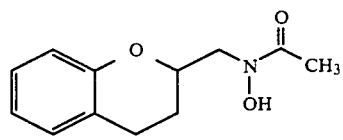

m.p.: 120.5°-120.8° C.

IR: (KBr): 3150, 2845, 1618, 1600, 1584, 749 cm$^{-1}$.

NMR: (270 MHz, CDCl$_3$) δ: 8.45(br. s, 1H), 7.12-7.04(m, 2H), 6.88-6.75(m, 2H), 4.42-1.5(m, 1H), 4.0-3.75(m, 2H), 2.95-2.80(m, 2H), 2.20(s, 3H), 2.15-1.95(m, 1H), 1.85-1.75(m, 1H).

EXAMPLE 16

N-Hydroxy-N-(2-indan-1ylethyl)urea

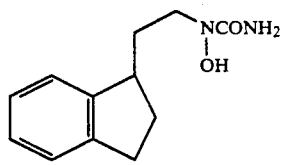

m.p.: 89.0°-89.9° C.

IR: (KBr) ν 3480, 1635.

NMR: (270 MHz, CDCl$_3$) δ: 7.12-7.25 (m, 4H), 5.26 (br s, 2H), 3.55-3.76 (m, 2H), 3.07-3.21 (m, 1H), 2.76-2.97 (m, 2H), 2.14-2.38 (m, 2H), 1.63-1.79 (m, 3H).

EXAMPLE 17

N-Hydroxy-N-(2-phenyl-3,4-dihydro-2H-benzopyran-6-yl)methylurea

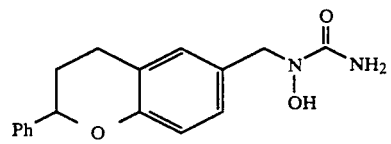

m.p.: 163.8°-164.5° C.

E.A.: Calcd.: C, 68.44% H, 6.08% N, 9.39%; Found: C, 68.68% H, 6.21% N, 9.10%.

IR: (KBr, cm$^{-1}$) 3525, 3415, 1647, 1490.

NMR: (270 MHz, DMSO-d$_6$) δ 9.25 (s, 1H), 7.31-7.46 (m, 5H), 7.02 (br s, 2H), 6.76 (d, 1H, J=6 Hz), 6.29 (br s, 2H), 5.10 (dd, 1H, J=2, 10 Hz), 4.41 (s, 2H), 2.88-3.03 (m, 1H), 2.63-2.76 (m, 1H), 2.11-2.22 (m, 1H), 1.91-2.07 (m, 1H).

EXAMPLE 18

N-Hydroxy-N-(6-methoxyindan-1-yl)urea

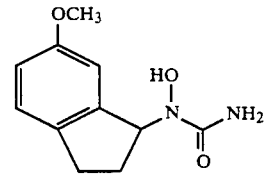

m.p.: 160.0°-160.4° C.

IR: (KBr): 3465, 3190, 1653, 1572, 1489, 1451 cm$^{-1}$.

NMR: (270 MHz, DMSO-d$_6$) δ: 8.95(s, 1H), 7.08(d, J=8 Hz, 1H), 6.75(dd, J=2 and 8 Hz, 1H), 6.72(d, J=2 Hz, 1H), 6.42(s, 2H), 5.62(t, J=7 Hz, 1H), 3.71(s, 3H), 2.9-2.78(m, 1H), 2.7-2.6(m, 1H), 2.2-2.0(m, 2H).

EXAMPLE 19

N-Hydroxy-N-(6-methoxyindan-1-yl)acetamide

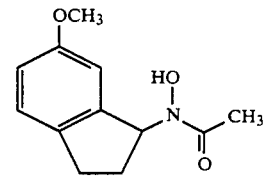

m.p.: 153.2°-154.2° C.
IR: (KBr): 2850, 1610, 1586 cm$^{-1}$.
NMR: (270 MHz, DMSO-d$_6$) δ: 9.45(s, 1H), 7.13(d, J=8 Hz, 1H), 6.78(dd, J=2 and 8 Hz, 1H), 6.64(d, J=2 Hz, 1H), 5.90(t, 7 Hz, 1H), 3.71(s, 3H), 2.95-2.82(m, 1H), 2.76-2.64(m, 1H), 2.25-2.0(m, 2H), 2.06(s, 3H).

EXAMPLE 20

N-Hydroxy-N-(5-benzyloxyindan-1-yl)acetamide

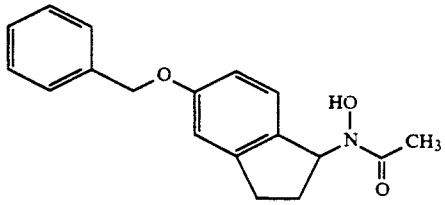

m.p.: 143.5°-144.0° C.
IR: (KBr): 3200, 1603 cm$^{-1}$.
NMR: (270 MHz, DMSO-d$_6$) δ: 9.40(s, 1H), 7.45-7.31(m, 5H), 7.01(d, J=8 Hz, 1H), 6.88(d, J=2 Hz, 1H), 6.81(dd, J=2 and 8 Hz, 1H), 5.89(t, J=7 Hz, 1H), 5.08(s, 2H), 3.00-2.86(m, 1H), 2.82-2.66(m, 1H), 2.25-2.0(m, 2H), 2.04(s, 3H).

EXAMPLE 21

N-Hydroxy-N-(5-benzyloxyindan-1-yl)urea

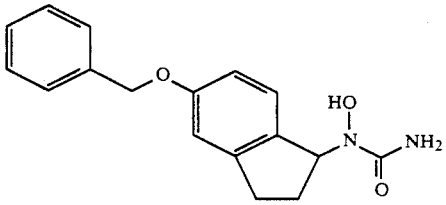

m.p.: 165.0°-166.5° C.
IR: (KBr): 3455, 3260, 1651, 1617, 1573, 1419, 734 cm$^{-1}$.
NMR: (270 MHz, DMSO-d$_6$) delta: 8.90(s,1H), 7.45-7.3(m,5H), 7.06 (d, J=8 Hz, 1H), 6.85(d, J=2 Hz, 1H), 6.80 (dd, J=2 and 8 Hz, 1H), 6.36(s, 2H), 5.59(t, J=7 Hz, 1H), 5.06(s, 2H), 2.96-2.8(m, 1H), 2.76-2.62(m, 1H), 2.22-2.04(m, 2H).

EXAMPLE 22

N-(3,4-Dihydro-2H-benzopyran-6-yl)methyl-N-hydroxyurea

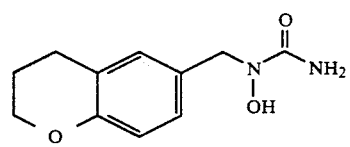

m.p.: 140°-142° C.
IR: (KBr, cm$^{-1}$) 3440, 1639, 1497.
NMR: (270 MHz, DMSO-d$_6$) δ 9.22 (s, 1H), 6.94-6.97 (m, 2H), 6.65 (d, 1H, J=9 Hz), 6.27 (br s, 2H), 4.37 (s, 2H), 4.09 (t, 2H, J=5 Hz), 2.70 (t, 2H, J=6 Hz), 1.86-1.94 (m, 2H).

EXAMPLE 23

N-Hydroxy-N-(6-methylindan-1-yl)acetamide

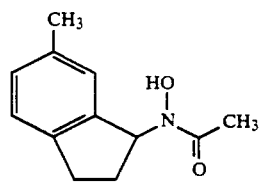

m.p.: 159.2°-160.4° C.
IR: (KBr): 2850, 1600, 1430 cm$^{-1}$.
NMR: (270 MHz, DMSO-d$_6$) δ: 9.44(s, 1H), 7.11(d, J=8 Hz, 1H), 7.02(d, J=8 Hz, 1H), 6.92(s, 1H), 5.93(t, J=7 Hz, 1H), 2.96-2.84(m, 1H), 2.8-2.65(m, 1H).

EXAMPLE 24

N-(3,4-Dihydro-2H-benzopyran-6-yl)methyl-N-hydroxyacetamide

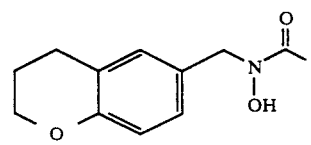

m.p.: 115°-118° C.
IR: (KBr, cm$^{-1}$) 3435, 2935, 1619, 1599, 1499, 1251.
NMR: (270 MHz, CDCl$_3$) δ 8.34 (br s, 1H), 6.94-7.06 (m, 2H), 6.78 (d, 1H, J=8 Hz), 4.70 (s, 2H), 4.18 (t, 2H, J=5 Hz), 2.78 (t, 2H, J=6 Hz), 2.18(s, 3H), 1.94-2.06(m, 2H).

EXAMPLE 25

N-Hydroxy-N-(5-methylindan-1-yl)urea

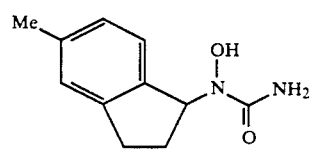

m.p.: 172.9°-174.6° C.
IR: ν (KBr): 3460, 1660, 1570, 1460 cm$^{-1}$.
NMR: δ (DMSO-d$_6$): 8.89 (s, 1H), 7.08-6.93 (m, 3H), 6.36 (s, 2H), 5.62 (t, J=7.7 Hz, 1H), 2.95-2.80 (m, 1H), 2.77-2.62 (m, 1H), 2.26 (s, 3H), 2.23-1.98 (m, 2H).

EXAMPLE 26

N-Hydroxy-N-(5-chloroindan-1-yl)urea

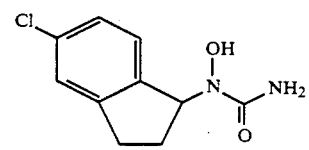

m.p.: 169.4°-170.8° C.
IR: ν (KBr): 3480, 1655, 1530 cm$^{-1}$.
NMR: δ (DMSO-d$_6$): 9.01 (s, 1H), 7.28-7.11 (m, 3H), 6.43 (s, 2H), 5.63 (t, J=7.5 Hz, 1H), 2.97-2.85 (m, 1H), 2.82-2.59 (m, 1H), 2.28-2.04 (m, 2H).

EXAMPLE 27

N-Hydroxy-N-{1-(3-methoxybenzyl)-1,2,3,4-tetrahydroquinolin-6-yl}methylacetamide

STRUCTURE:

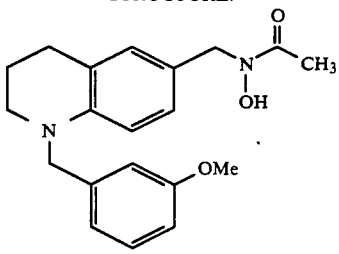

mp: 96.3°–96.5° C./dec.
IR (KBr) cm$^{-1}$: 1610, 1600.
NMR (DMSO) δ: 9.70 (s, 1H), 7.19–7.27 (m, 1H), 6.75–6.84 (m, 5H), 6.38 (d, J=8.2 Hz, 1H), 4.45 (s, 2H), 4.43 (s, 2H), 3.72 (s, 3H), 3.25–3.53*(2H), 2.66–2.75 (m, 2H), 1.98 (s, 3H), 1.84–1.97 (m, 2H)
*This peak was hidden by H$_2$O in DMSO-d$_6$

EXAMPLE 28

N-{1-(4-Chlorobenzyl)-1,2,3,4-tetrahydroquinolin-6-yl}methyl-N-hydroxyacetamide

STRUCTURE:

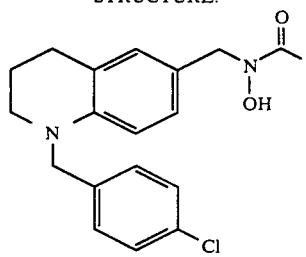

mp: 163°–166° C. (dec).
IR (KBr) cm$^{-1}$: 3145, 2940, 2875, 1612, 1602, 1509 cm$^{-1}$.
NMR (CDCl$_3$) δ: 8.31 (br s, 1H), 7.26 (d, 2H, J=1.5 Hz), 7.19 (d, 2H, J=1.5 Hz), 6.91 (br s, 2H), 6.40 (d, 1H, J=8 Hz), 4.64 (s, 2H), 4.42 (s, 2H), 3.35 (t, 2H, J=6 Hz), 2.80 (t, 2H, J=6 Hz), 2.17 (s, 3H), 2.03 (quin, 2H, J=6 Hz).

EXAMPLE 29

N-Hydroxy-N-{5-(2-quinolylmethoxy)indan-1-yl}urea

STRUCTURE:

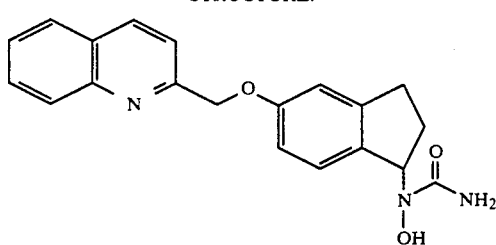

mp: 182.8°–184.1° C.
IR (KBr) cm$^{-1}$: 3480, 3200, 1650, 1570, 1490, 1430, 1330, 1280, 1140, 920.
NMR (DMSO-d$_6$) δ: 8.92(s, 1H), 8.40(d, J=8.43 Hz, 1H), 8.00(t, J=8.43 Hz, 2H), 7.78(m, 1H), 7.62(m, 2H), 7.07(d, J=8.43 Hz, 1H), 6.87(m, 2H), 6.35(s, 2H), 5.59(m, 1H), 5.33(s, 2H), 2.85(m, 1H), 2.69(m, 1H), 2.13(m, 2H).

EXAMPLE 30

N-Hydroxy-N-{1-(3-methoxybenzyl)-8-chloro-1,2,3,4-tetrahydroquinolin-6-yl}methylacetamide

STRUCTURE:

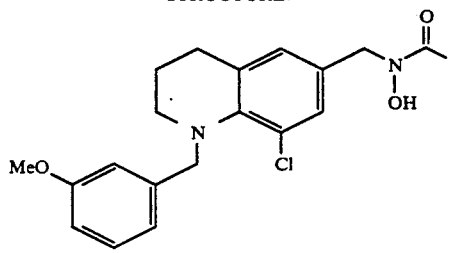

mp: amorphous.
IR (KBr) cm$^{-1}$: 2930, 1610, 1475, 1255 cm$^{-1}$.
NMR (CDCl$_3$) δ: 9.90 (s, 1H), 7.28 (dd, 1H, J=8.1, 7.7 Hz), 7.08–7.13 (m, 3H), 6.95 (d, 1H, J=1.8 Hz), 6.85 (dd, 1H, J=8.1, 1.8 Hz), 4.75 (s, 2H), 4.12 (s, 2H), 3.75 (s, 3H), 2.82–2.86 (m, 2H), 2.74–2.79 (m, 2H), 2.03 (s, 3H), 1.73–1.79 (br, 2H).

EXAMPLE 31

N-Hydroxy-N-[4-{(3,4-dihydro-2H-benzopyran)6-yl}3-buten-2-acetamide

STRUCTURE:

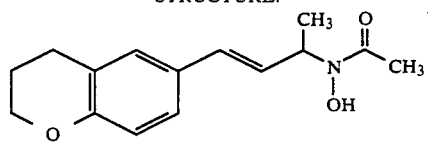

mp: 90°–93° C.
IR: ν (Nujol): 1610, 1590, 1490, 1240, 1170, 1060, 1005, 970, 820 cm$^{-1}$.
NMR: δ (CDCl$_3$-DMSO-d$_6$): 8.95(s, 1H), 7.10(d, J=8.4 Hz, 1H), 7.05(s, 1H), 6.70(d, J=8.4 Hz, 1H), 6.42 (d, J=15.7 Hz, 1H), 6.12 (d d, J=6.6, 15.7 Hz, 1H), 5.29 (m, 1H), 4.16 (t, J=5.1 Hz, 2H), 2.75 (t, J=6.2 Hz, 2H), 2.14 (s, 3H), 1.99 (m, 2H), 1.37 (br d, 3H).

EXAMPLE 32

N-Hydroxy-N-(4-phenoxyindan-1-yl)acetamide

STRUCTURE:

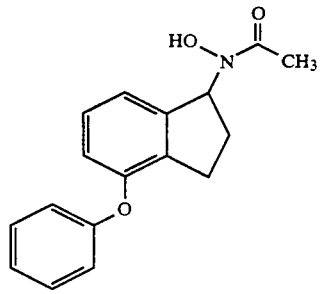

mp: 141.4°–143.1° C.
IR: ν (KBr): 2850, 1585, 1465, 1245, 770 cm$^{-1}$.

NMR: δ (DMSO-d₆): 9.51 (s, 1H), 7.36 (t, J=8 Hz, 2H), 7.22 (t, J=8 Hz, 1H), 7.10 (t, J=8 Hz, 1H), 695 (d, J=8 Hz, 3H), 6.79 (d, J=8 Hz, 1H), 6.01 (t, J=7 Hz, 1H), 2.9-2.76 (m, 1H), 2.66-2.56 (m, 1H), 2.3-2.0 (m, 2H), 2.07 (s, 3H).

EXAMPLE 33

N-Hydroxy-N-(5-phenoxyindan-1-yl)acetamide

STRUCTURE:

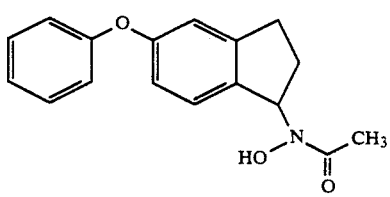

mp: 111.0°-111.5° C.
IR: ν (KBr): 3450, 3150, 2700, 1605, 1590, 1485, 1250, 780, 695 cm⁻¹.
NMR: δ (DMSO-d₆): 9.48 (s, 1H), 7.38 (t, J=8 Hz, 2H), 7.14 (t, J=8 Hz, 2H), 6.98 (dd, J=8 and 2 Hz, 2H), 6.85 (s, 1H), 6.83 (d, J=8 Hz, 1H), 5.94 (t, J=7 Hz, 1H), 3.0-2.9 (m, 1H), 2.85-2.7 (m, 1H), 2.3-2.05 (m, 2H), 2.05 (s, 3H).

EXAMPLE 34

N-Hydroxy-N-{1-(4-fluorobenzyl)-1,2,3,4-tetrahydroquinolin-6-yl}methylurea

STRUCTURE:

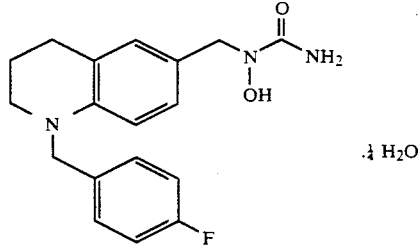

¼ H₂O m.p.: 141.4°-141.6° C./dec.
IR: ν (KBr): 3500, 1645.
NMR: δ (DMSO): 9.14 (s, 1H), 7.23-7.32 (m, 2H), 7.09-7.18 (m, 2H), 6.77-6.85 (m, 2H), 6.39 (d, J=8.1 Hz, 1H), 6.20 (s, 2H), 4.44 (s, 2H), 4.29 (s, 2H), 3.23-3.37*(2H). 2.70 (t, J=6.2 Hz, 2H), 1.85-1.95 (m, 2H).
*This peak was hidden by H₂O is DMSO-d₆

EXAMPLE 35

N-Hydroxy-N-{1-(1-benzoyl-1,2,3,4-tetrahydroquinolin-6-yl)ethyl}urea

STRUCTURE:

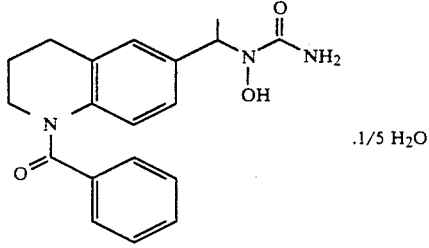

.1/5 H₂O m.p.: 180.7°-181.0° C./dec.
IR: ν (KBr): 3450, 1670, 1610.
NMR: δ (DMSO): 9.01 (s, 1H), 7.32-7.43 (m, 5H), 7.15 (s, 1H), 6.84-6.90 (m, 1H), 6.75-6.81 (m, 1H), 6.26 (s, 2H), 5.20 (q, J=7.0 Hz, 1H), 3.71 (t, J=6.2 Hz, 2H), 2.79 (t, J=6.6 Hz, 2H), 1.86-1.99 (m, 2H), 1.34(d, J=7.0 Hz, 3H).

EXAMPLE 36

N-Hydroxy-N-{1-(1-benzoyl-1,2,3,4-tetrahydroquinolin-7-yl)ethyl}urea

STRUCTURE:

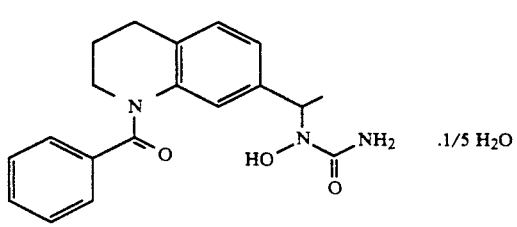

.1/5 H₂O m.p.: 161.4°-161.7° C./dec.
IR: ν (KBr): 3500, 1652, 1610.
NMR: δ (DMSO); 8.85 (s, 1H), 7.26-7.43 (m, 5H), 7.08 (d, J=8.1 Hz, 1H), 6.93 (dd, J=7.7 Hz, 1.5 Hz, 1H), 6.69 (s, 1H), 6.16 (s, 2H), 4.94 (q, J=7.0 Hz, 1H), 3.64-3.86 (m, 2H), 2.78 (t, J=6.6 Hz, 2H), 1.88-2.01 (m, 2H), 0.91 (d, J=7.0 Hz, 3H).

EXAMPLE 37

N-Hydroxy-N-(1-allyl-1,2,3,4-tetrahydroquinolin-6-yl)methylurea

STRUCTURE:

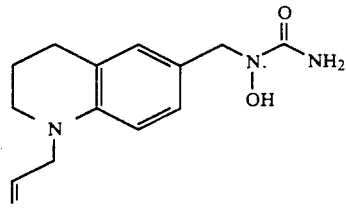

m.p.: 114.3°-114.6° C./dec.
IR: ν (KBr): 3440, 1665, 1640, 1610.
NMR: δ (DMSO): 9.14 (s, 1H), 6.85 (d, J=8.4 Hz, 1H), 6.81 (s, 1H), 6.45 (d, J=8.4 Hz, 1H), 6.21 (s, 2H), 5.73-5.89 (m, 1H), 5.08-5.19 (m, 2H), 4.30 (s, 2H), 3.79-3.88 (m, 2H), 3.21 (t, J=5.7 Hz, 2H), 2.66 (t, J=6.2 Hz, 2H), 1.80-1.91 (m, 2H).

EXAMPLE 38

N-Hydroxy-N-{1-(4-methybenzyl)-1,2,3,4-tetrahydroquinolin-6-yl}methylurea

STRUCTURE:

-continued

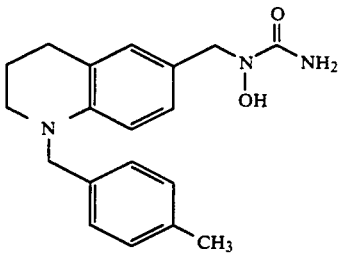

m.p.: 156.6°-156.8° C./dec.
IR: ν (KBr): 3520, 3400, 1650, 1615.
NMR: δ (DMSO):
9.13 (s, 1H), 7.12 (s, 4H), 6.82 (s, 1H), 6.78 (d, J=8.4 Hz, 1H), 6.38 (d, J=8.4 Hz, 1H), 6.19 (s, 2H), 4.40 (s, 2H), 4.28 (s, 2H), 3.25-3.41*(2H), 2.70 (t, J=6.2 Hz, 2H), 2.26 (s, 3H), 1.85-1.96 (m, 2H).
*This peak was hidden by H₂O in DMSO-d₆.

EXAMPLE 39

N-Hydroxy-N-(1-benzyl-1,2,3,4-tetrahydroquinaldin-6-yl)methylurea

STRUCTURE:

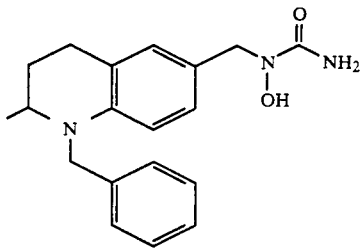

m.p.: 141.8°-142.1° C./dec.
IR: ν (KBr): 3420, 1673, 1640, 1615.
NMR: δ (DMSO): 9.13 (s, 1H), 7.17-7.36 (m, 5H), 6.87 (s, 1H), 6.76 (d, J=8.4 Hz, 1H), 6.22 (d, J=8.4 Hz, 1H), 6.19 (s, 2H), 4.47 (d, J=5.1 Hz, 2H), 4.28 (s, 2H), 3.50-3.65 (m, 1H), 2.58-2.90 (m, 2H), 1.71-2.00 (m, 2H), 1.11 (d, J=6.6 Hz, 3H).

EXAMPLE 40

N-Hydroxy-N-{1-(1-phenylethyl)-1,2,3,4-tetrahydroquinolin-6-yl}methylurea

STRUCTURE:

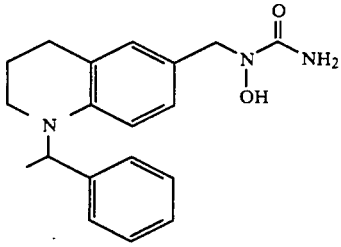

m.p.: 125.0°-125.3° C./dec.
IR: ν (KBr): 3520, 3400, 1650, 1615.
NMR: δ (DMSO): 9.14(s, 1H), 7.18-7.38 (m, 5H), 6.79-6.87 (m, 2H), 6.59 (d, J=9.2 Hz, 1H), 6.21 (s, 2H), 5.08 (q, J=7.0 Hz, 1H), 4.30 (s, 2H), 2.94-3.25 (m, 2H), 2.61-2.71 (m, 2H), 1.65-1.92 (m, 2H), 1.5 (d, J=7.0 Hz, 3H).

EXAMPLE 41

N-Hydroxy-N-{1-(2-phenylethyl)-1,2,3,4-tetrahydroquinolin-6-yl}methylurea

STRUCTURE:

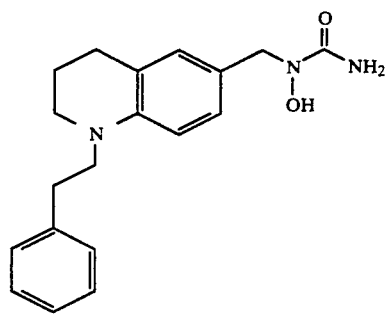

m.p.: 132.4°-132.8° C./dec.
IR: ν (KBr): 3480, 1641.
NMR: δ (DMSO):
9.26(s, 1H), 7.14-7.33 (m, 5H), 6.91 (d, J=8.4 Hz, 1H), 6.80 (s, 1H), 6.56 (d, J=8.4 Hz, 1H), 6.20 (s, 2H), 4.31 (s, 2H), 3.34-3.45 (m, 2H), 3.14 (t, J=5.3 Hz, 2H), 2.69-2.80 (m, 2H), 2.60 (t, J=6.2 Hz, 2H), 1.66-1.83 (m, 2H).

EXAMPLE 42

N-Hydroxy-N-{1-(3-methoxybenzyl)-1,2,3,4-tetrahydroquinolin-6-yl}methylurea-HCl-2/3H₂O

STRUCTURE:

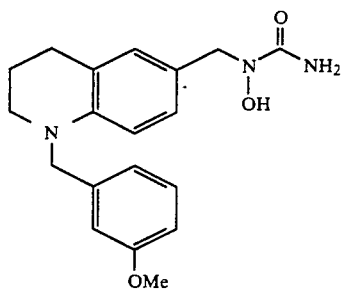

m.p.: 97.4°-100.2° C./dec.
IR: ν (KBr): 1650.
NMR: δ (DMSO): 7.24 (t, J=8.1 Hz, 1H), 6.77-6.90 (m, 5H), 6.43-6.53 (m, 1H), 4.45 (s, 2H), 4.32 (s, 2H), 3.71 (s, 3H), 3.33 (t, J=5.5 Hz, 2H), 2.72 (t, J=5.9 Hz, 2H), 1.85-1.99(m, 2H) ppm.
*This peak was hidden by H₂O in DMSO-d₆.

EXAMPLE 43

N-Hydroxy-N-{1-(3-methoxybenzyl)-1,2,3,4-tetrahydroquinolin-6-yl}methylurea

STRUCTURE:

-continued

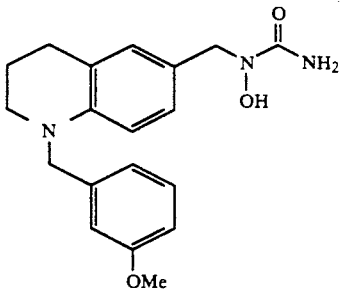

m.p.: 120.7°–121.0° C./dec.
IR: ν (KBr): 3500, 1640.
NMR: δ (DMSO): 9.13 (s, 1H), 7.16–7.24 (m, 1H), 6.72–6.83 (m, 5H), 6.34 (d, J=8.4 Hz, 1H), 6.17 (s, 2H), 4.40 (s, 2H), 4.27 (s, 2H), 3.68 (s, 3H), 3.17–3.46*(2H), 2.68(t, J=6.2 Hz, 2H), 1.80–1.95 (m, 2H).
*This peak was hidden by H₂O in DMSO-d₆.

EXAMPLE 44

N-Hydroxy-N-{1-(2-methoxybenzyl)-1,2,3,4-tetrahydroquinolin-6-yl}methylurea

STRUCTURE:

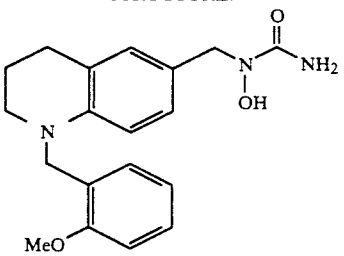

m.p.: 104.2°–104.8° C./dec.
IR: ν (KBr): 3420, 1670.
NMR: δ (DMSO): 9.14 (s, 1H), 7.22 (t, J=7.4 Hz, 1H), 7.01 (d, J=7.7 Hz, 2H), 6.82–6.89 (m, 2H), 6.77 (d, J=8.1 Hz, 1H), 6.15–6.24 (m, 3H), 4.37 (s, 2H), 4.29 (s, 2H), 3.83 (s, 3H), 3.25–3.45*(2H), 2.73 (t, J=6.0 Hz, 2H), 1.86–1.98 (m, 2H).
*This peak was hidden by H₂O in DMSO-d₆.

EXAMPLE 45

N-Hydroxy-N-{1-(3-trifluoromethylbenzyl)-1,2,3,4-tetrahydroquinolin-6-yl}methylurea

STRUCTURE:

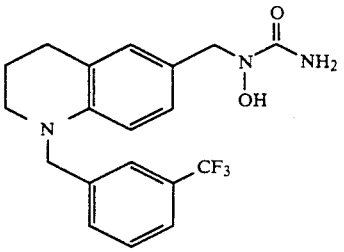

m.p.: 133.7°–133.8° C./dec.
IR: ν (KBr): 3500, 1618.
NMR: δ (DMSO): 9.16 (s, 1H), 7.50–7.63 (m, 4H), 6.85 (s, 1H), 6.80 (d, J=8.4 Hz, 1H), 6.37 (d, J=8.4 Hz, 1H), 6.21 (s, 2H), 4.56 (s, 2H), 4.30 (s, 2H), 3.27–3.46*(2H), 2.73 (t, J=6.2 Hz, 2H), 1.86–1.99 (m, 2H).
*This peak was hidden by H₂O in DMSO-d₆.

EXAMPLE 46

N-Hydroxy-N-{1-(3,5-dimethoxybenzyl)-1,2,3,4-tetrahydroquinolin-6-yl}methylurea

STRUCTURE:

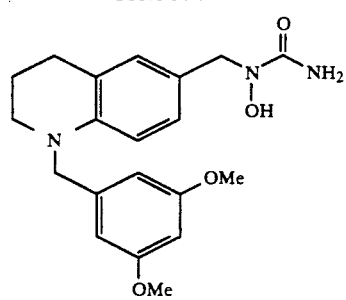

m.p.: 152.5°–153.0° C./dec.
IR: ν (KBr): 3500, 1652.
NMR: δ (DMSO): 9.16 (s, 1H), 6.83 (s, 1H), 6.80 (d, J=8.1 Hz, 1H), 6.33–6.41 (m, 4H), 6.20 (s, 2H), 4.38 (s, 2H), 4.29 (s, 2H), 3.70 (s, 6H), 3.28–3.51*(2H), 2.71 (t, J=6.0 Hz, 2H), 1.83–1.96 (m, 2H).
*This peak was hidden by H₂O in DMSO-d₆.

EXAMPLE 47

N-Hydroxy-N-{1-(3-chlorobenzyl)-1,2,3,4-tetrahydroquinolin-6-yl}methylurea

STRUCTURE:

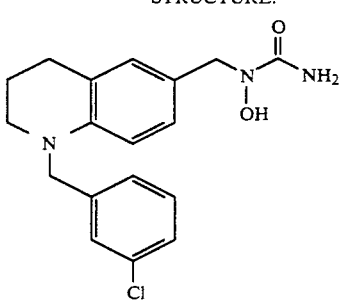

.¼ H₂O m.p.: 119.7°–121.6° C./dec.
IR: ν (KBr): 3480, 1638.
NMR: δ (DMSO): 9.15 (s, 1H), 7.35 (t, J=7.3 Hz, 1H), 7.25–7.32 (m, 2H), 7.20 (d, J=7.3 Hz, 1H), 6.84 (s, 1H), 6.81 (d, J=8.4 Hz, 1H), 6.35 (d, J=8.4 Hz, 1H), 6.21 (s, 2H), 4.47 (s, 2H), 4.30 (s, 2H), 3.26–3.45*(2H), 2.72 (t, J=6.2 Hz, 2H), 1.85–1.93 (m, 2H).
*This peak was hidden by H₂O in DMSO-d₆.

EXAMPLE 48

N-Hydroxy-N-{1-(3-pentyloxybenzyl)-1,2,3,4-tetrahydroquinolin-6-yl}methylurea

STRUCTURE:

-continued

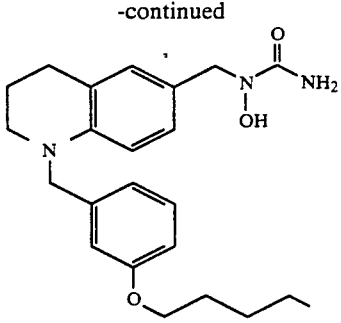

m.p.: 13.7°–131.8° C./dec.
IR: ν (KBr): 3500, 1640.
NMR: δ (DMSO): 9.14 (s, 1H), 7.17–7.25 (m, 1H), 6.74–6.85 (m, 5H), 6.37 (d, J=8.1 Hz, 1H), 6.20 (s, 2H), 4.41 (s, 2H), 4.29 (s, 2H), 3.91 (t, J=6.4 Hz, 2H), 3.26–3.50*(2H), 2.71 (t, J=6.2 Hz, 2H), 1.85–1.96 (m, 2H).
*This peak was hidden by H$_2$O in DMSO-d$_6$.

EXAMPLE 49

N-Hydroxy-N-{1-(3-fluorobenzyl)-1,2,3,4-tetrahydroquinolin-6-yl}methylurea

STRUCTURE:

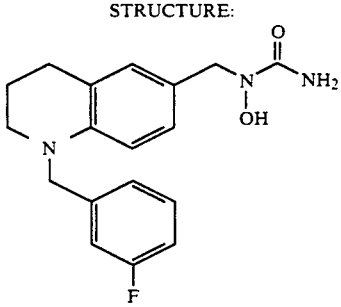

m.p.: 123.5°–123.9° C./dec.
IR: ν (KBr): 3420, 1662, 1615.
NMR: δ (DMSO): 9.15 (s, 1H), 7.32–7.42 (m, 1H), 6.99–7.12 (m, 3H), 6.84 (s, 1H), 6.80 (d, J=8.4 Hz, 1H), 6.35 (d, J=8.4 Hz, 1H), 6.20 (s, 2H), 4.47 (s, 2H), 4.29 (s, 2H), 3.24–3.53*(2H), 2.72 (t, J=6.2 Hz, 2H), 1.86–1.98 (m, 2H),
*This peak was hidden by H$_2$O in DMSO-d$_6$.

EXAMPLE 50

N-Hydroxy-N-{1-(2-fluorobenzyl)-1,2,3,4-tetrahydroquinolin-6-yl}methylurea

STRUCTURE:

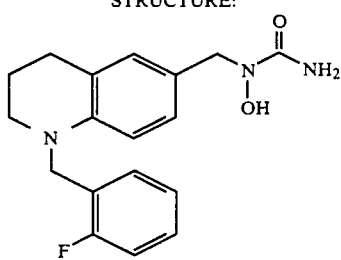

m.p.: 134.7°–134.9° C./dec.
IR: ν (KBr): 3500, 3400, 1650, 1615.
NMR: δ (DMSO): 9.14 (s, 1H), 7.08–7.35 (m, 4), 6.84 (s, 1H), 6.81 (d, J=8.1 Hz, 1H), 6.37 (d, J=8.4 Hz, 1H), 6.21 (s, 2H), 4.50 (s, 2H), 4.29 (s, 2H), 3.28–3.38 (m, 2H), 2.72 (t, J=6.2 Hz, 2H), 1.86–1.97 (m, 2H).

EXAMPLE 51

N-Hydroxy-N-[1-{3-(2-propoxy)benzyl]-1,2,3,4-tetrahydroquinolin-6-yl}methylurea

STRUCTURE:

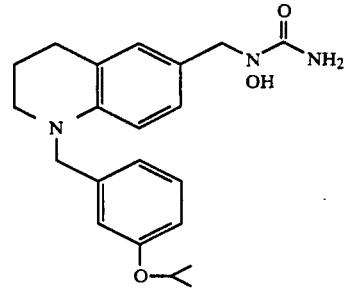

m.p.: 134.4°–134.5° C./dec.
IR: ν (KBr): 3500, 1640.
NMR: δ (DMSO): 9.13 (s, 1H), 7.19 (t, J=7.7 Hz, 1H), 6.72–6.85 (m, 5H), 6.38 (d, J=8.1 Hz, 1H), 6.20 (s, 2H), 4.49–4.61 (m, 1H), 4.41 (s, 2H), 4.29 (s, 2H), 3.26–3.36 (m, 2H), 2.71 (t, J=6.0 Hz, 2H), 1.84–1.93 (m, 2H), 1.23 (d, J=6.2 Hz, 6H).

EXAMPLE 52

N-Hydroxy-N-{1-(3-allyloxybenzyl)-1,2,3,4-tetrahydroquinolin-6-yl}methylurea

STRUCTURE:

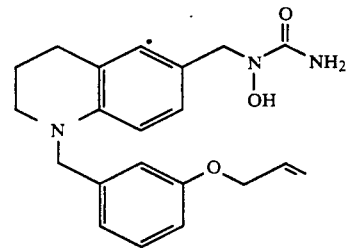

m.p.: 120.8°–121.5° C./dec.
IR: ν (KBr): 3490, 1630.
NMR: δ (DMSO): 9.13 (s, 1H), 7.18–7.26 (m, 1H), 6.76–6.85 (m, 5H), 6.37 (d, J=8.1 Hz, 1H), 6.20 (s, 2H), 6.01 (ddt, J=17.2 Hz, 10.2 Hz, 5.1 Hz, 1H), 5.36 (dtt, J=17.2 Hz, 1.8 Hz, 1H), 5.23 (dtt, J=10.2 Hz, 1.8 Hz, 1.8 Hz, 1H), 4.52 (ddd, J=5.1 Hz, 1.5 Hz, 1.5 Hz, 2H), 4.42 (s, 2H), 4.29 (s, 2H). 3.24–3.41*(2H), 2.71 (t, J=6.4 Hz, 2H), 1.85–1.97 (m, 2H).
*This peak was hidden by H$_2$O in DMSO-d$_6$.

EXAMPLE 53

N-Hydroxy-N-{1-(3-methoxyphenylethyl)-1,2,3,4-tetrahydroquinolin-6-yl}methylurea

STRUCTURE:

-continued

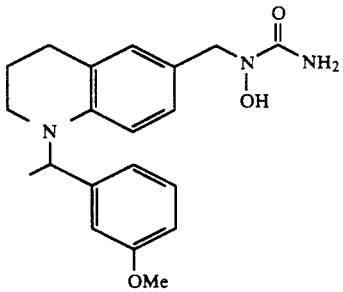

m.p.: 126.0°–126.7° C./dec.
IR: ν (KBr): 3500, 3450, 3200, 1670, 1640, 1615.
NMR: δ (DMSO): 9.13 (s, 1H), 7.25 (t, J=7.7 Hz, 1H), 6.77–6.91 (m, 5H), 6.57 (d, J=9.2 Hz, 1H), 6.20 (s, 2H), 5.03 (q, J=6.5 Hz, 1H), 4.30 (s, 2H), 3.77 (s, 3H), 3.25–3.44*(2H), 2.67–2.71 (m, 2H), 1.68–1.91 (m, 2H), 1.48 (d, J=6.5 Hz, 3H).
*This peak was hidden by H₂O in DMSO-d₆.

EXAMPLE 54

N-Hydroxy-N-{1-(3-cyanobenzyl)-1,2,3,4-tetrahydroquinolin-6-yl}methylurea

STRUCTURE:

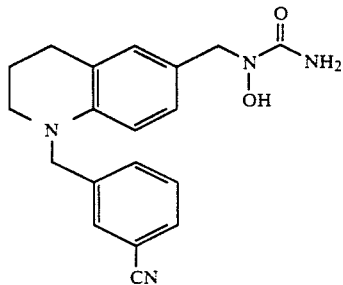

m.p.: 140.2°–141.6° C./dec.
IR: ν (KBr): 3430, 3340, 2220, 1640.
NMR: δ (DMSO): 9.14 (s, 1H), 7.71 (ddd, J=7.7 Hz, 1.4 Hz, 1.4 Hz, 1H), 7.67 (s, 1H), 7.59 (ddd, J=7.7 Hz, 1.4 Hz, 1.4 Hz, 1H), 7.53 (t, J=7.7 Hz, 1H), 6.84 (d, J=2.2 Hz, 1H), 6.80 (dd, J=8.1 Hz, 2.2 Hz, 1H), 6.33 (d, J=6.1 Hz, 1H), 6.21 (s, 2H), 4.52 (s, 2H), 4.29 (s, 2H), 3.24–3.43*(2H), 2.66–2.78 (m, 2H), 1.87–1.98 (m, 2H).
*This peak was hidden by H₂O in DMSO-d₆.

EXAMPLE 55

N-Hydroxy-N-{1-(3-phenylpropyl)-1,2,3,4-tetrahydroquinolin-6-yl}methylurea

STRUCTURE:

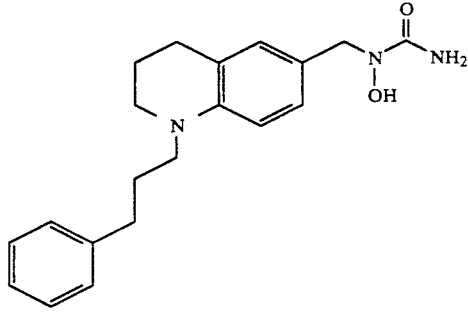

m.p.: 113.1°–113.8° C./dec.

IR: ν (KBr): 3500, 1635.
NMR: δ (DMSO): 9.13 (s, 1H), 7.14–7.33 (m, 5H), 6.83 (dd, J=8.2 Hz, 1.9 Hz, 1H), 6.78 (d, J=1.9 Hz, 1H), 6.39 (d, J=8.2 Hz, 1H), 6.20 (s, 2H), 4.29 (s, 2H), 3.15–3.28 (m, 4H), 2.56–2.69 (m, 4H), 1.71–1.90 (m, 4H).

EXAMPLE 56

N-Hydroxy-N-{1-(4-cyanobenzyl)-1,2,3,4-tetrahydroquinolin-6-yl}methylurea

STRUCTURE:

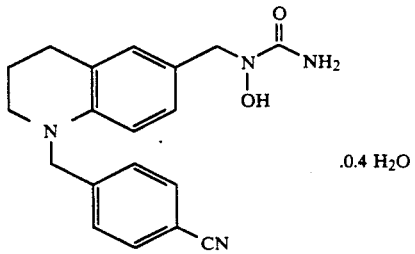

.0.4 H₂O m.p.: 141.7°–143.2° C./dec.
IR: ν (KBr): 3500, 2220, 1640.
NMR: δ (DMSO): 9.16 (s, 1H), 7.78 (d, J=8.4 Hz, 2H), 7.43 (d, J=8.4 Hz, 2H), 6.85 (d, J=1.8 Hz, 1H), 6.78 (dd, J=8.4 Hz, 1.8 Hz, 1H), 6.29 (d, J=8.4 Hz, 1H), 6.21 (s, 2H), 4.55 (s, 2H), 4.29 (s, 2H), 3.25–3.56*(2H), 2.72 (t, J=6.4 Hz, 2H), 1.87–1.99 (m, 2H).
*This peak was hidden by H₂O in DMSO-d₆.

EXAMPLE 57

N-Hydroxy-N-(1,2,3,4-tetrahydroquinolin-6-yl)methylurea

STRUCTURE:

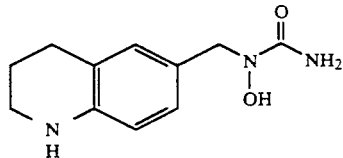

m.p.: 121.0°–121.6° C./dec.
IR: ν (KBr): 3490, 3390, 1640.
NMR: δ (DMSO): 9.11 (s, 1H), 6.73–6.79 (m, 2H), 6.34 (d, J=8.8 Hz, 1H), 6.19 (s, 2H), 5.51 (s, 1H), 4.27 (s, 2H), 3.09–3.18 (m, 2H), 2.62 (t, J=6.2 Hz, 2H), 1.70–1.82 (m, 2H).

EXAMPLE 58

N-Hydroxy-N-{1-(3-methoxycarbonylbenzyl)-1,2,3,4-tetrahydroquinolin-6-yl}methylurea

STRUCTURE:

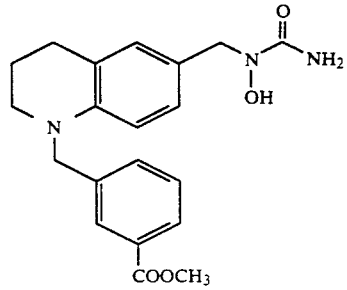

m.p.: 146.5°–147.3° C./dec.

IR: ν (KBr): 3490, 3390, 1720, 1710, 1650, 1630.

NMR: δ (DMSO): 9.14 (s, 1H), 7.86 (s, 1H), 7.80–7.85 (m, 1H), 7.51–7.56 (m, 1H), 7.47 (t, J=7.5 Hz, 1H), 6.85 (d, J=1.1 Hz, 1H), 6.79 (dd, J=8.1 Hz, 1.1 Hz, 1H), 6.36 (d, J=8.1 Hz, 1H), 6.29 (s, 2H), 4.53 (s, 2H), 4.29 (s, 2H), 3.83 (s, 3H), 3.26–3.40 (m, 2H), 2.68–2.78 (m, 2H), 1.87–1.98 (m, 2H).

EXAMPLE 59

N-Hydroxy-N-[1-{2-(3-methoxyphenyl)ethyl}-1,2,3,4-tetrahydroquinolin-6-yl]methylurea

STRUCTURE:

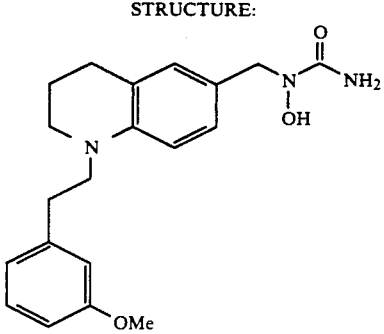

m.p.: 108.0°–108.7° C./dec.

IR: ν (KBr): 3420, 3330, 1675, 1640, 1615.

NMR: δ (DMSO): 9.15 (s, 1H), 7.21 (t, J=8.1 Hz, 1H), 6.92 (dd, J=8.4 Hz, 1.8 Hz, 1H), 6.80–6.86 (m, 3H), 6.77 (dd, J=8.1 Hz, 2.2 Hz, 1H), 6.59 (d, J=8.4 Hz, 1H), 6.21 (s, 2H), 4.32 (s, 2H), 3.74 (s, 3H), 3.37–3.48 (m, 2H), 3.14–3.22 (m, 2H), 2.70–2.79 (m, 2H), 2.63 (t, J=6.2 Hz, 2H), 1.75–1.86 (m, 2H).

EXAMPLE 60

N-Hydroxy-N-{1-(3-methoxymethylbenzyl)-1,2,3,4-tetrahydroquinolin-6-yl}methylurea

STRUCTURE:

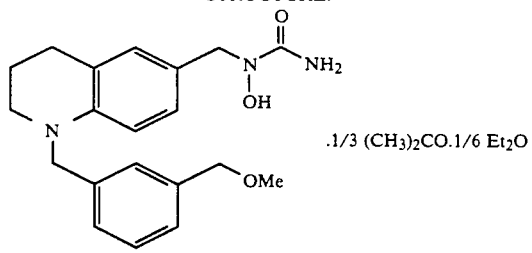

.1/3 (CH₃)₂CO.1/6 Et₂O m.p.: 94.9°–95.2° C./dec.

IR: ν (KBr): 3420, 1645.

NMR: δ (DMSO): 9.13 (s, 1H), 7.29 (t, J=7.5 Hz, 1H), 7.12–7.22 (m, 3H), 6.83 (d, J=1.9 Hz, 1H), 6.79 (dd, J=8.4 Hz, 1.9 Hz, 1H), 6.38 (d, J=8.4 Hz, 1H), 6.20 (s, 2H), 4.45 (s, 2H), 4.38 (s, 2H), 4.29 (s, 2H), 3.28–3.39*(2H), 3.27 (s, 3H), 2.71 (t, J=6.4 Hz, 2H), 1.85–1.96 (m, 2H).

*This peak was hidden by H₂O in DMSO-d₆.

EXAMPLE 61

N-Hydroxy-N-{1-(2-cyanobenzyl)-1,2,3,4-tetrahydroquinolin-6yl}methylurea

STRUCTURE:

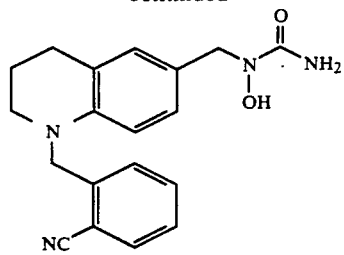

m.p.: 140.3°–140.6° C./dec.

IR: ν (KBr): 3400, 1675, 1640, 1615.

NMR: δ (DMSO): 9.15 (s, 1H), 7.86 (d, J=7.7 Hz, 1H), 7.64 (td, J=7.7 Hz, 1.0 Hz, 1H), 7.44 (t, J=7.7 Hz, 1H), 7.37 (d, J=7.7 Hz, 1H), 6.87 (s, 1H), 6.80 (d, J=8.5 Hz, 1H), 6.29 (d, J=8.5 Hz, 1H), 6.21 (s, 2H), 4.63 (s, 2H), 4.30 (s, 2H), 3.24–3.43*(2H), 2.74 (t, J=6.0 Hz, 2H), 1.87–2.00 (m, 2H).

*This peak was hidden by H₂O in DMSO-d₆.

EXAMPLE 62

N-Hydroxy-N-{1-(3-carbamoylbenzyl)-1,2,3,4-tetrahydroquinolin-6-yl}methylurea

STRUCTURE:

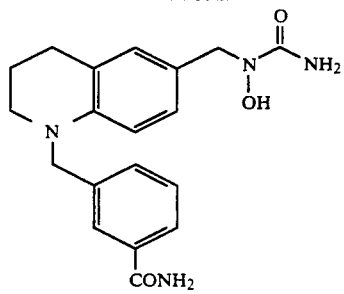

m.p.: 117.6°–120.0° C./dec.

IR: ν (KBr): 3490, 3330, 3180, 1670, 1620.

NMR: δ (DMSO): 9.13 (s, 1H), 7.95 (s, 1H), 7.68–7.80 (m, 2H), 7.30–7.43 (m, 3H), 6.84 (d, J=2.2 Hz, 1H), 6.79 (dd, J=8.4 Hz, 2.2 Hz, 1H), 6.37 (d, J=8.4 Hz, 1H), 6.20 (s, 2H), 4.49 (s, 2H), 4.29 (s, 2H), 3.26–3.44*(2H), 2.72 (t, J=6.2 Hz, 2H), 1.87–1.98 (m, 2H).

*This peak was hidden by H₂O in DMSO-d₆.

EXAMPLE 63

N-(1-Phenyl-1,2,3,4-tetrahydroquinolin-6-yl)methyl-N-hydroxyurea

STRUCTURE:

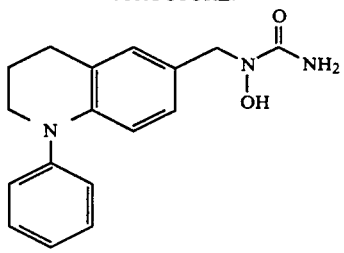

m.p.: 89°–90° C.

IR: ν (KBr): 3440, 1646, 1595, 1566, 1498, 1490 cm⁻¹.

NMR: δ (CDCl₃): 7.06–7.38 (m, 5H), 7.04 (br s, 1H), 6.91 (dd, 1H, J=8, 2 Hz), 6.68 (d, 1H, J=8 Hz), 5.92 (br s, 1H), 5.20 (br s, 2H), 4.56 (s, 2H), 3.61 (t, 2H, J=6 Hz), 2.84 (t, 2H, J=6 Hz), 2.04 (quin, 2H, J=6 Hz).

EXAMPLE 64

N-Hydroxy-N-(3-methoxy-1-phenyl-1,2,3,4-tetrahydroquinolin-6-yl)methylurea

STRUCTURE:

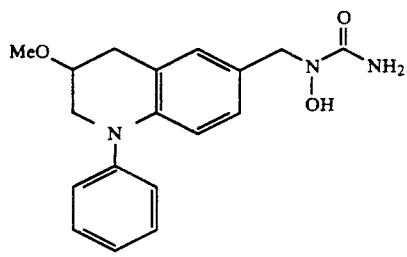

m.p.: 132.1°–132.5° C./dec.
IR: ν (KBr): 3480, 1652.
NMR: δ (DMSO): 9.22 (s, 1H), 7.35 (t, J=7 Hz, 2H), 7.20 (d, J=8 Hz, 2H), 7.06 (t, J=7 Hz, 1H), 6.98 (s, 1H), 6.84 (d, J=8 Hz, 1H), 6.60 (d, J=8 Hz, 1H), 6.25 (s, 2H), 4.36 (s, 2H), 3.76–3.85 (m, 1H), 3.70 (dd, J=9 Hz, 1 Hz, 1H), 3.51 (dd, J=13 Hz, 6 Hz, 1H), 3.26 (s, 3H), 3.04 (dd, J=16 Hz, 4Hz, 1H), 2.75 (dd, J=16 Hz, 6 Hz, 1H).

EXAMPLE 65

N-Hydroxy-N-(3-allyloxy-1-phenyl-1,2,3,4-tetrahydroquinolin-6-yl)methylurea

STRUCTURE:

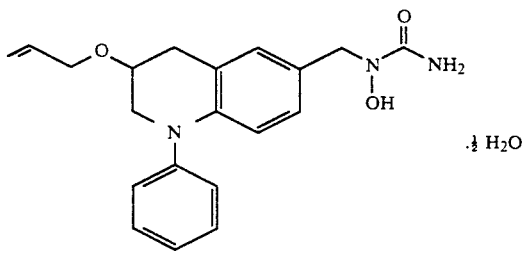

.¼ H$_2$O m.p.: (amorphous solid).
IR: ν (KBr): 3500, 1650.
NMR: δ (DMSO): 9.23 (s, 1H), 7.34 (t, J=7.3 Hz, 2H), 7.19 (d, J=7.3 Hz, 2H), 7.06 (t, J=7.0 Hz, 1H), 6.99 (s, 1H), 6.84 (d, J=8.4 Hz, 1H), 6.61 (d, J=8.4 Hz, 1H), 6.26 (s, 2H), 5.84 (ddt, J=15.4 Hz, 10.3 Hz, 5.1 Hz, 1H), 5.19 (dtt, J=15.4 Hz, 1.5 Hz, 1.5 Hz, 1H), 5.08 (d, J=10.3 Hz, 1H), 4.36 (s, 2H), 3.87–4.07 (m, 3H), 3.71 (dd, J=13 Hz, 4 Hz, 1H), 3.52 (dd, J=13 Hz, 6 Hz, 1H), 3.05 (dd, J=15 Hz, 4 Hz, 1H), 2.76 (dd, J=15 Hz, 6 Hz, 1H).

EXAMPLE 66

N-Hydroxy-N-{7-methoxy-1-(3-methoxybenzyl)-1,2,3,4-tetrahydroquinolin-6-yl}methylurea

STRUCTURE:

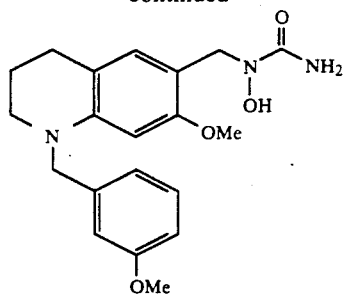

m.p.: 124.2°–126.8° C./dec.
IR: ν (KBr): 3500, 1640, 1620.
NMR: δ (DMSO): 9.11 (s, 1H), 7.24 (t, J=8.6 Hz, 1H), 6.74–6.89 (m, 4H), 6.20 (s, 2H), 6.09 (s, 1H), 4.46 (s, 2H), 4.34 (s, 2H), 3.72 (s, 3H), 3.53 (s, 3H), 3.27–3.35 (m, 2H), 2.62 (t, J=2.6 Hz, 2H), 1.82–1.94 (m, 2H).

EXAMPLE 67

N-Hydroxy-N-{7-chloro-1-(3-methoxybenzyl)-1,2,3,4-tetrahydroquinolin-6-yl}methylurea

STRUCTURE:

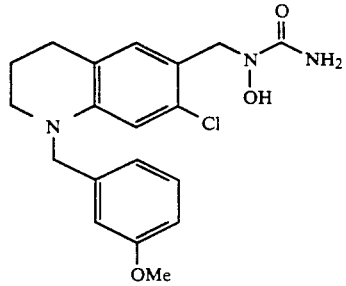

m.p.: 157.0°–158.1° C./dec.
IR: ν (KBr): 3500, 1650, 1610.
NMR: δ (DMSO): 9.27 (s, 1H), 7.25 (t, J=8.1 Hz, 1H), 6.93 (s, 1H), 6.76–6.84 (m, 3H), 6.38 (s, 1H), 6.32 (s, 2H), 4.45 (s, 2H), 4.44 (s, 2H), 3.72 (s, 3H), 3.25–3.41*(2H), 2.69 (t, J=6.2 Hz, 2H), 1.84–1.96 (m, 2H).

*This peak was hidden by H$_2$O in DMSO-d$_6$.

EXAMPLE 68

N-Hydroxy-N-{1-(3-difluoromethoxybenzyl)-1,2,3,4-tetrahydroquinolin-6-yl}methyl-N'-ethylurea

STRUCTURE:

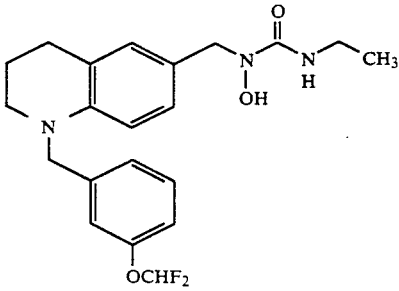

m.p.: 113.9°–114.2° C./dec.
IR: ν (KBr): 3450, 1635.
NMR: δ (DMSO): 9.05 (s, 1H), 7.37 (t, J=8.1 Hz, 1H), 7.21 (t, J=74.2 Hz, 1H), 7.11 (d, J=8.1 Hz, 1H), 7.00–7.06 (m, 2H), 6.76–6.85 (m, 3H), 6.36 (d, J=8.4 Hz, 1H), 4.47 (s, 2H), 4.28 (s, 2H), 3.27–3.39*(2H), 3.06 (quint, J=6.3 Hz, 2H), 2.67–2.77 (m, 2H), 1.86–1.97 (m, 2H), 0.99 (t, J=7.1 Hz, 3H).

*This peak was hidden by H₂O in DMSO-d₆.

EXAMPLE 69

N-Hydroxy-N-{1-(3-difluoromethoxybenzyl)-1,2,3,4-tetrahydroquinolin-6-yl}methylurea

STRUCTURE:

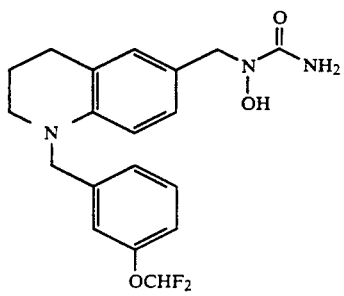

m.p.: 115.3°–115.6° C./dec.

IR: ν (KBr): 3410, 3330, 1675, 1640, 1620.

NMR: δ (DMSO): 9.14 (s, 1H), 7.37 (t, J=8.4 Hz, 1H), 7.21 (t, J=74.2 Hz, 1H), 7.11 (d, J=7.7 Hz, 1H), 7.00–7.06 (m, 2H), 6.84 (d, J=2.2 Hz, 1H), 6.80 (dd, J=8.4 Hz, 2.2 Hz, 1H), 6.36 (d, J=8.4 Hz, 1H), 6.21 (s, 2H), 4.47 (s, 2H), 4.29 (s, 2H), 3.28–3.39*(2H), 2.71 (t, J=6.0 Hz, 2H), 1.85–1.98 (m, 2H).

EXAMPLE 70

N-(1-(4-Chlorobenzyl)-1,2,3,4-tetrahydroquinolin-6-yl)methyl-N-hydroxyurea

STRUCTURE:

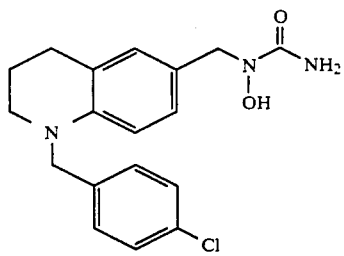

mp: 145°–146° C. (dec).

IR cm⁻¹: 3400, 1644, 1552, 1508 cm⁻.

NMR (CDCl₃) δ: 7.28 (d, 2H, J=1.5 Hz), 7.18 (d, 2H, J=1.5 Hz), 6.94–7.00 (m, 2H), 6.40 (d, 1H, J=8 Hz), 5.53 (br s, 1H), 5.17 (br s, 2H), 4.54 (s, 2H), 4.42 (s, 2H), 3.35 (t, 2H, J=6 Hz), 2.80 (t, 2H, J=6 Hz), 2.03 (quin, 2H, J=6 Hz).

EXAMPLE 71

N-(1-(4-Methoxybenzyl)-1,2,3,4-tetrahydroquinolin-6-yl)methyl-N-hydroxyurea

STRUCTURE:

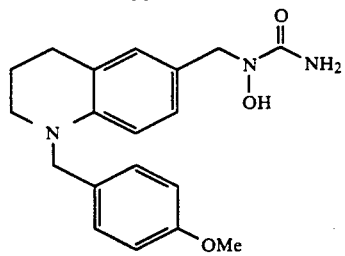

mp: 140°–143° C. (dec).

IR (KBr) cm⁻¹: 3515, 3390, 1647, 1615, 1554, 1512, 1458, 1250 cm⁻¹.

NMR (DMSO) δ: 9.13 (br s, 1H), 7.17 (d, 2H, J=1.5 Hz), 6.87 (d, 2H, J=1.5 Hz), 6.78–6.84 (m, 2H), 6.42 (d, 1H, J=8 Hz), 4.38 (s, 2H), 4.29 (s, 2H), 3.31 (s, 3H), 3.30 (br s, 2H), 2.69 (t, 2H, J=6 Hz), 1.89 (quin, 2H, J=6 Hz).

EXAMPLE 72

N-Hydroxy-N-{1-(3-trifluoromethylbenzyl)-8-fluoro-1,2,3,4-tetrahydroquinolin-6-yl}methylurea

STRUCTURE:

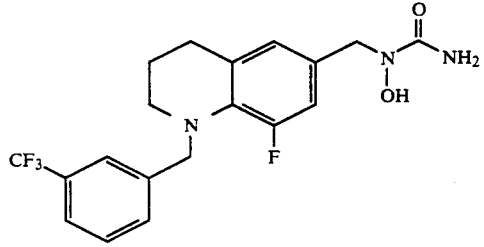

m.p.: 148.5°–149.5° C.

IR: ν (KBr): 3500, 1645, 1625, 1325, 1130 cm⁻¹.

NMR: δ (DMSO): 9.31 (s, 1H), 7.56–7.72 (m, 4H), 6.83 (dd, 1H, J=13.9, 1.8 Hz), 6.78 (br, 1H), 6.33 (s, 2H), 4.38 (s, 2H), 4.34 (s, 2H), 2.93–3.01 (m, 2H), 2.72 (t, 2H, J=6.2 Hz), 1.74–1.83 (br, 2H).

EXAMPLE 73

N-Hydroxy-N-{1-(3-difluoromethoxybenzyl)-8-fluoro-1,2,3,4-tetrahydroquinolin-6-yl}methylurea

STRUCTURE:

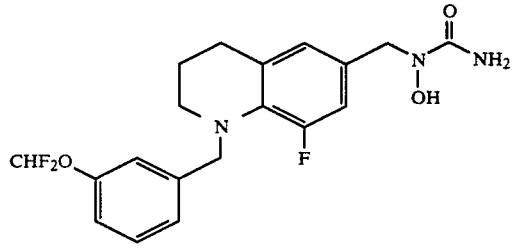

m.p.: 109°–110° C.

IR: ν (KBr): 3495, 1645, 1625, 1115 cm⁻¹.

NMR: δ (DMSO): 9.31 (s, 1H), 7.40 (dd, 1H, J=7.9, 7.9 Hz), 7.22–7.26 (m, 1H), 7.22 (t, 1H, J=74.2 Hz), 7.17 (br, 1H), 7.05–7.09 (m, 1H), 6.77–6.85 (m, 2H), 6.33 (s, 2H), 4.38 (s, 2H), 4.28 (s, 2H), 2.98–3.02 (2H), 2.70 (t, 2H, J=6.2 Hz), 1.77 (br, 2H).

EXAMPLE 74

N-Hydroxy-N-[3-{1-(3-methoxybenzyl)-1,2,3,4-tetrahydroquinolin-6-yl}propyl]urea

STRUCTURE:

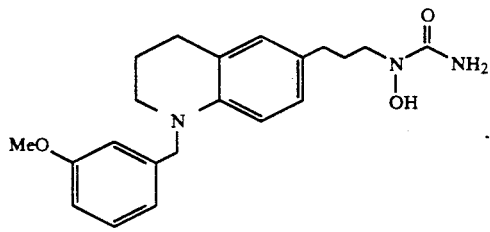

m.p.: 95°-96° C.
IR: ν (KBr): 3465, 1630, 1515 cm⁻¹.
NMR: δ (DMSO): 9.19 (s, 1H), 7.19-7.25 (m, 1H), 6.68-6.83 (m, 5H), 6.35 (d, 1H, J=8.0 Hz), 6.22 (s, 2H), 4.40 (s, 2H), 3.71 (s, 3H), 3.26-3.32 (4H), 2.70 (t, 2H, J=6.4 Hz), 2.36 (t, 2H, J=7.5 Hz), 1.88-1.93 (m, 2H), 1.65-1.71 (m, 2H).

EXAMPLE 75

N-Hydroxy-N-{1-(3-cyanobenzyl)-8-fluoro-1,2,3,4-tetrahydroquinolin-6-yl}methylurea

STRUCTURE:

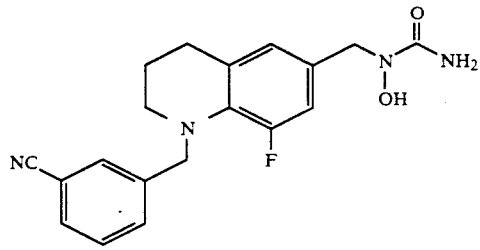

m.p.: 141°-142° C.
IR: ν (KBr): 3500, 2230, 1640, 1630, 1495 cm⁻¹.
NMR: δ (DMSO): 9.32 (s, 1H) 7.71-7.79 (m, 3H), 7.57 (dd, 1H, J=7.7, 7.7 Hz), 6.77-6.85 (m, 2H), 6.33 (s, 2H), 4.38 (s, 2H) 4.31 (s, 2H), 3.00 (t, 2H, J=5.3 Hz), 2.71 (t, 2H, J=6.2 Hz), 1.72-1.85 (m, 2H).

EXAMPLE 76

N-Hydroxy-N-{1-cyclohexylmethyl-1,2,3,4-tetrahydroquinolin-6-yl}methylurea

STRUCTURE:

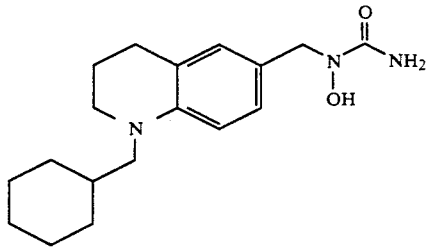

m.p.: 111°-112° C.
IR: ν (KBr): 3490, 2925, 1640, 1515 cm⁻¹.
NMR: δ (DMSO): 9.13 (s, 1H), 6.85(dd, 1H, J=8.4, 2.2 Hz), 6.78 (d, 1H, J=2.2 Hz), 6.40 (d, 1H, J=8.4 Hz), 6.20 (s, 2H), 4.29 (s, 2H), 3.24 (t, 2H, J=5.5 Hz), 3.00 (d, 2H, J=6.6 Hz), 2.64 (t, 2H, J=6.2 Hz), 1.66-1.83 (m, 8H), 1.10-1.25 (m, 3H), 0.85-0.95 (m, 2H).

EXAMPLE 77

N-Hydroxy-N-{1-(pyridin-3-yl)methyl-1,2,3,4-tetrahydroquinolin-6-yl}methylurea

STRUCTURE:

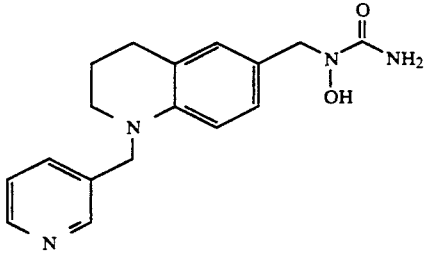

m.p.: 62°-68° C. (amorphous).
IR: ν (KBr): 3490, 1655, 1650, 1515, 785 cm⁻¹.
NMR: δ (DMSO): 9.15 (s, 1H), 8.48 (d, 1H, J=1.8 Hz), 8.44 (dd, 1H, J=4.8, 1.5 Hz), 7.63 (ddd, 1H, J=7.7, 1.8, 1.5 Hz), 7.33 (dd, 1H, J=7.7, 4.8 Hz), 6.79-6.84 (m, 2H), 6.43 (d, 1H, J=8.4 Hz), 6.21 (s, 2H), 4.51 (s, 2H), 4.29 (s, 2H), 3.30-3.37 (2H), 2.71 (t, 2H, J=6.2 Hz), 1.87-1.967 (m, 2H).

EXAMPLE 78

N-Hydroxy-N-{1-(3-methoxybenzyl)-7-methyl-1,2,3,4-tetrahydroquinolin-6-yl}methylurea

STRUCTURE:

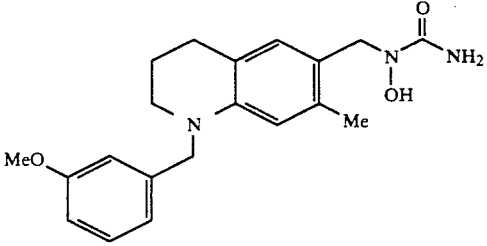

m.p.: 142°-143° C.
IR: ν (KBr): 3500, 1635, 1516, 1484, 1337 cm⁻¹.
NMR: δ (DMSO): 9.11 (s, 1H), 7.20-7.26 (m, 1H), 6.78-6.83 (m, 4H), 6.28 (s, 1H), 6.20 (s, 2H), 4.42 (s, 2H), 4.33 (s, 2H), 3.72 (s, 3H), 3.29-3.33 (2H), 2.66 (m, 2H), 2.08 (s, 3H), 1.86-1.90 (br, 2H).

EXAMPLE 79

N-Hydroxy-N-{1-(3-methoxybenzyl)-5-methyl-1,2,3,4-tetrahydroquinolin-6-yl}methylurea

STRUCTURE:

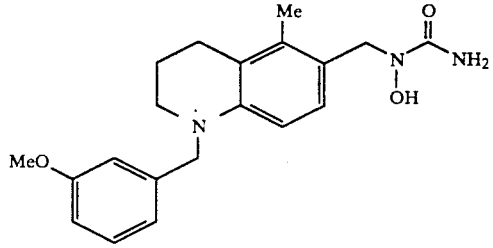

m.p.: 123.5°-125° C.

IR: ν (KBr): 3490, 1640, 1575, 1455 cm⁻¹.

NMR: δ (DMSO): 9.02 (s, 1H), 7.19–7.25 (m, 1H), 6.75–6.83 (m, 4H), 6.28 (d, 1H, J=8.4 Hz), 6.18 (s, 2H), 4.41 (s, 2H), 4.37 (s, 2H), 3.71 (s, 3H), 3.27–3.31 (2H), 2.61–2.66 (m, 2H), 2.10 (s, 3H), 1.92–1.96 (br, 2H).

EXAMPLE 80

N-Hydroxy-N-{1-(3-methoxybenzyl)-8-methyl-1,2,3,4-tetrahydroquinolin-6-yl}methylurea

STRUCTURE:

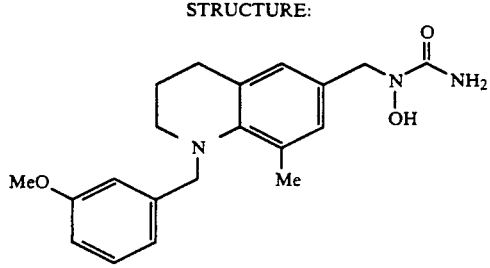

m.p.: 138°–139° C.

IR: ν (KBr): 3505, 3390, 1660, 1600, 1260 cm⁻¹.

NMR: δ (DMSO): 9.24 (s, 1H), 7.29 (dd, 1H, J=7.9, 7.9 Hz), 7.05–7.08 (m, 2H), 6.82–6.89 (m, 3H), 6.28 (s, 2H), 4.38 (s, 2H), 3.94 (s, 2H), 3.76 (s, 3H), 2.84–2.87 (m, 2H), 2.70–2.75 (m, 2H), 2.22 (s, 3H), 1.7–1.76 (br, 2H).

EXAMPLE 81

N-Hydroxy-N-{1-(3-methoxybenzyl)-7-fluoro-1,2,3,4-tetrahydroquinolin-6-yl}methylurea

STRUCTURE:

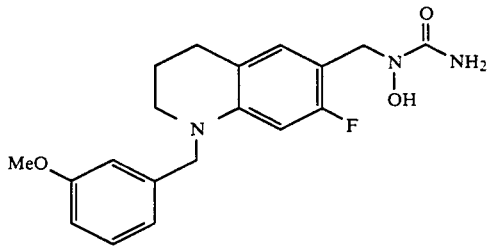

m.p.: 150°–151° C.

IR: ν (KBr): 3490, 3200, 1645, 1520, 1280 cm⁻¹.

NMR: δ (DMSO): 9.20 (s, 1H), 7.21–7.27 (m, 1H), 6.88 (d, 1H, J=8.8 Hz), 6.79–6.81 (m, 3H), 6.26 (s, 2H), 6.15 (d, 1H, J=13.6 Hz), 4.44 (s, 2H), 4.35 (s, 2H), 3.72 (s, 3H), 3.29–3.37 (2H), 2.65–2.69 (m, 2H), 1.87–1.92 (m, 2H).

EXAMPLE 82

N-Hydroxy-N-{1-(3-methoxybenzyl)-8-fluoro-1,2,3,4-tetrahydroquinolin-6-yl}methylurea

STRUCTURE:

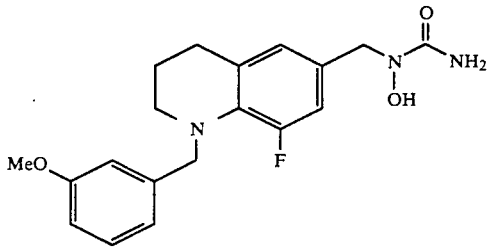

m.p.: 141°–142° C.

IR: ν (KBr): 3505, 3390, 1660, 1494, 1260 cm⁻¹.

NMR: δ (DMSO): 9.30 (s, 1H), 7.25 (dd, 1H, J=8.1, 7.7 Hz), 6.90–6.94 (m, 2H), 6.76–6.84 (m, 3H), 6.32 (s, 2H), 4.37 (s, 2H), 4.25 (s, 2H), 3.73 (s, 3H), 2.89–3.02 (m, 2H), 2.66–2.71 (m, 2H), 1.73–1.77 (m, 2H).

EXAMPLE 83

N-Hydroxy-N-{1-(3-methoxybenzyl)-8-chloro-1,2,3,4-tetrahydroquinolin-6-yl}methylurea

STRUCTURE:

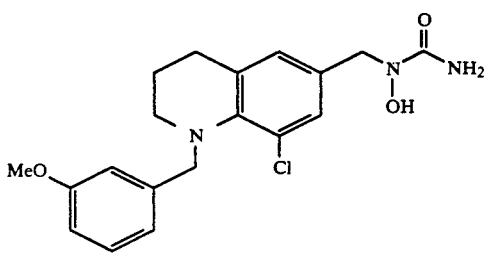

m.p.: 95°–97° C. (amorphous).

IR: ν (KBr): 3490, 1650, 1470 cm⁻¹.

NMR: δ (DMSO): 9.36 (s, 1H), 7.28 (dd, 1H, J=8.1, 7.7 Hz), 7.08–7.15 (m, 3H), 6.96 (d, 1H, J=1.8 Hz), 6.85 (dd, 1H, J=8.1, 1.8 Hz), 6.36 (s, 2H), 4.41 (s, 2H), 4.11 (s, 2H), 3.75 (s, 3H), 2.82–2.86 (m, 2H), 2.76 (t, 2H, J=6.6 Hz), 1.73–1.77 (br, 2H).

EXAMPLE 84

N-Hydroxy-N-{1-(thiophen-2-yl)methyl-1,2,3,4-tetrahydroquinolin-6-yl}methylurea

STRUCTURE:

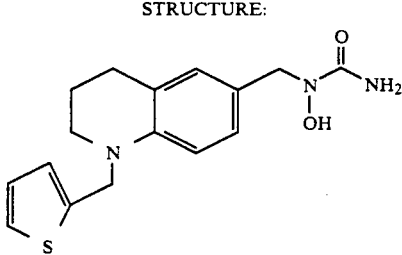

m.p.: 135°–136° C. (dec.).

IR: ν (KBr): 3470, 1625, 1515 cm⁻¹.

NMR: δ (DMSO): 9.16 (s, 1H), 7.35 (dd, 1H, J=4.8, 1.5 Hz), 7.01 (br, 1H), 6.96 (dd, 1H, J=4.8, 3.7 Hz), 6.82–6.87 (m, 2H), 6.64 (d, 1H, J=8.4 Hz), 6.21 (s, 2H), 4.62 (s, 2H), 4.30 (s, 2H), 3.28–3.32 (2H), 2.66 (t, 2H, J=6.7 Hz), 1.85–1.90 (br, 2H).

EXAMPLE 85

N-Hydroxy-N-{1-(3-methoxybenzyl)-5-fluoro-1,2,3,4-tetrahydroquinolin-6-yl}methylurea

STRUCTURE:

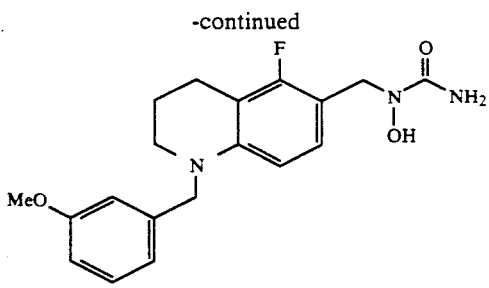

m.p.: 141°–142° C.

IR: ν (KBr): 3460, 1645, 1635, 1435 cm⁻¹.

NMR: δ (DMSO): 9.19 (s, 1H), 7.20–7.26 (m, 1H), 6.87 (dd, 1H, J=8.6, 8.6 Hz), 6.78–6.82 (m, 3H), 6.27 (d, 1H, J=8.6 Hz), 6.24 (s, 2H), 4.45 (s, 2H), 4.38 (s, 2H), 3.71 (s, 3H), 3.29–3.34 (2H), 2.67 (t, 2H), J=6.2 Hz), 1.88–1.93 (m, 2H).

EXAMPLE 86

N-Hydroxy-N-{2-(trans-indan-1-ylidene)ethyl}urea

STRUCTURE:

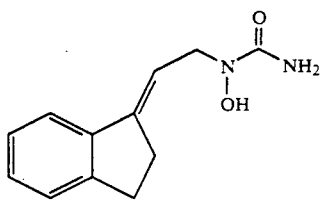

m.p.: 134°–136° C.

IR: ν (nujol): 1615, 1570, 1170, 1130, 860.

NMR: δ (CDCl₃-DMSO-d₆): 9.17 (s, 1H), 7.46 (m, 1H), 7.23 (m, 1H), 7.18 (m, 2H), 6.09 (m, 1H), 5.49 (s, 2H), 4.29 (d, j=7.3 Hz, 2H), 2.99 (t, j=5.1 Hz, 2H), 2.85 (d, j=5.1 Hz, 2H).

EXAMPLE 87

N-Hydroxy-N-(5-phenoxyindan-1-yl)urea

STRUCTURE:

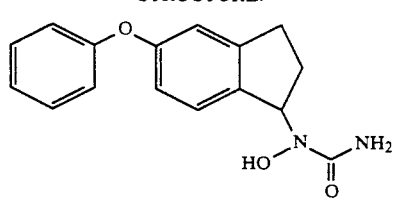

mp: 163.1°–164.0° C.

IR: ν (KBr): 3450, 3300, 1660, 1655, 1485, 1245 cm⁻¹.

NMR: δ (DMSO-d₆): 8.98 (s, 1H), 7.37 (t, J=8 Hz, 2H), 7.13 (t, J=8 Hz, 1H), 7.11 (t, J=8 Hz, 1H), 6.97 (d, J=8 Hz, 2H), 6.82 (s, 1H), 6.81 (d, J=8 Hz, 1H), 6.40 (s, 2H), 5.64 (t, J=7 Hz, 1H), 2.95–2.85 (m, 1H), 2.76–2.65 (m, 1H), 2.25–2.05 (m, 2H).

EXAMPLE 88

N-Hydroxy-N-(6-phenoxyindan-1-yl)urea

STRUCTURE:

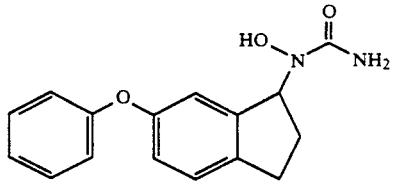

mp: 146.5°–147.7° C.

IR: ν (KBr): 3495, 3320, 1650, 1630, 1485, 1240, 690 cm⁻¹.

NMR: δ (DMSO-d₆): 9.01 (s, 1H), 7.33 (t, J=8 Hz, 2H), 7.21 (t, J=8 Hz, 1H), 7.09 (t, J=8 Hz, 1H), 6.94 (d, J=8 Hz, 2H), 6.86 (dd, J=8 and 2 Hz, 1H), 6.78 (d, J=2 Hz, 6.43 (s, 2H), 5.71 (t, J=8 Hz, 1H), 2.95–2.84 (m, 1H), 2.82–2.68 (m, 1H), 2.25–2.05 (m, 2H).

EXAMPLE 89

N-Hydroxy-N-(7-phenoxyindan-1-yl)urea

STRUCTURE:

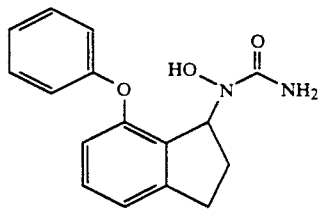

mp: 157.6°–158.8° C.

IR: ν (KBr): 3500, 3350, 3190, 1645, 1585, 1465, 1250, 765, 695 cm⁻.

NMR: δ (DMSO-d₆): 8.87 (s, 1H), 7.35 (dt, J=8 and 2 Hz, 2H), 7.17 (t, J=8 Hz, 1H), 7.1 (t, J=8 Hz, 1H), 7.01 (dd, J=8 and 2 Hz, 2H), 6.98 (t, J=7 Hz, 1H), 6.53 (d, J=8 Hz, 1H), 6.14 (s, 2H), 5.82 (dd, J=8 and 2 Hz, 1H), 3.1–295 (m, 1H), 2.85–2.7 (m, 1H), 2.3–2.15 (m, 1H), 2.08–1.96 (m, 1H).

EXAMPLE 90

N-Hydroxy-N-(4-phenoxyindan-1-yl)urea

STRUCTURE:

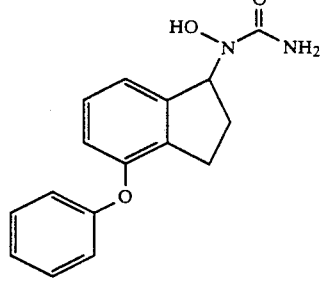

mp: 166.6°–168.1° C.

IR: ν (KBr): 3480, 3330, 3200, 1660, 1750, 1740, 1245, 780, 745 cm⁻¹.

NMR: δ (DMSO-d₆): 9.0 (s, 1H), 7.38 (t, J=8 Hz, 2H), 7.19 (t, J=8 Hz, 1H), 7.07 (t, J=8 Hz, 1H), 6.97 (t, J=8 Hz, 1H), 6.86 (d, J=8 Hz, 2H), 6.79 (d, J=8 Hz, 1H), 6.41 (s, 2H), 5.64 (t, J=7 Hz, 1H), 2.85–2.72 (m, 1H), 2.65–2.5 (m, 1H), 2.25–2.05 (m, 2H).

EXAMPLE 91

N-Hydroxy-N-[4-{(3,4-dihydro-2H-benzopyran)6-yl}3-buten-2-yl]urea

STRUCTURE:

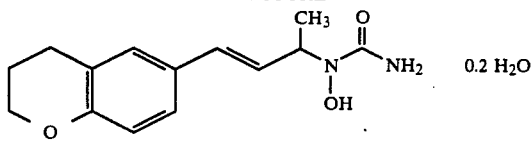 0.2 H₂O m.p.: 138°–140° C.

IR: ν (nujol) 3440, 1640, 1250, 1060, 970, 815 cm⁻¹.

NMR: δ (DMSO-d₆); 9.67 (s, 1H), 7.76 (m, 2H), 7.34 (d, J=8.8 Hz, 1H), 7.02 (d, J=15.1 Hz, 1H), 6.99 (s, 2H), 6.78 (d, J=6.6 Hz, 1H), 5.45 (m, 1H), 4.79 (t, J=6.2 Hz, 2H), 3.40 (t, J=6.2 Hz, 2H), 2.57 (m, 2H), 1.88 (d, J=7.0 Hz, 3H).

EXAMPLE 92

N-Hydroxy-N-{5-(3-methoxyphenoxy)indan-1-yl}urea

STRUCTURE:

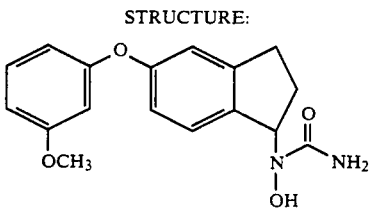

m.p.: 143.1°–144.6° C.

IR: ν (KBr): 3450, 3300, 3200, 2900, 1660, 1580, 1360, 1340, 1250, 870 cm⁻¹.

NMR: δ (DMSO-d₆): 8.97(s, 1H), 7.26(t, J=8.43 Hz, 1H), 7.14(d, J=8.43 Hz, 1H), 6.83(br.s, 1H), 6.82(d, J=6.60 Hz, 1H), 6.68(d, 9.16 Hz, 1H), 6.52(m, 2H), 6.40(br.s, 2H), 5.64(t, J=7.33 Hz, 1H), 3.73(s, 3H), 2.87(m, 1H), 2.74(m, 1H), 2.16(m, 2H).

EXAMPLE 93

N-Hydroxy-N-{5-(3-fluorophenoxy)indan-1-yl}urea

STRUCTURE:

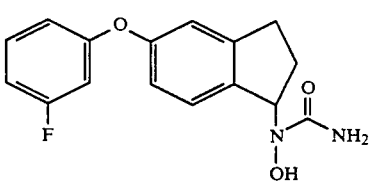

m.p.: 150.2°–153.2° C.

IR: ν (KBr): 3450, 3000–3400, 1680, 1610, 1580, 1480, 1260, 1140, 960 cm⁻¹.

NMR: δ (DMSO-d₆): 8.99(s, 1H), 7.39(m, 1H), 7.18(d, J=8.06 Hz, 1H), 6.87(m, 5H), 6.41(br.s, 2H), 5.65(t, J=7.33 Hz, 1H), 2.87(m, 1H), 2.74(m, 1H), 2.17(m, 2H).

EXAMPLE 94

N-Hydroxy-N-{5-(4-phenylphenoxy)indan-1-yl}urea

STRUCTURE:

-continued

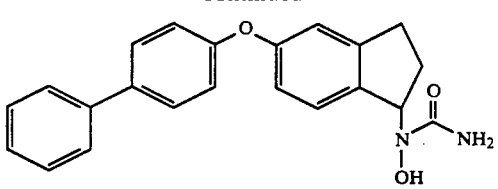

m.p.: 167.9°–169.2° C.

IR: ν (KBr): 3500, 3300, 2900, 1630, 1550, 1490, 1250, 1010, 980, 690 cm⁻¹.

NMR: δ (DMSO-d₆): 9.00(s, 1H), 7.65(m, 4H), 7.45(m, 2H), 7.34(m, 1H), 7.18(d, J=8.42 Hz, 1H), 7.05(m, 2H), 6.87(m, 2H), 6.42(br.s, 2H), 5.66(t, J=7.36 Hz, 1H), 2.91(m, 1H), 2.76(m, 1H), 2.17(m, 2H).

EXAMPLE 95

N-Hydroxy-N-{5-(3,4-dimethylenedioxyphenoxy)indan-1-yl}urea

STRUCTURE:

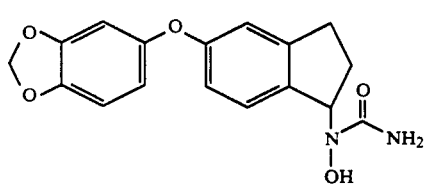

m.p.: 173.2°–174.0° C.

IR: ν (KBr): 3450, 3200, 2900, 1650, 1570, 1480, 1240, 1040, 920 cm⁻¹.

NMR: δ (DMSO-d₆): 8.95(s, 1H), 7.11(m, 1H), 6.89(d, J=8.42 Hz, 1H), 6.76(m, 2H), 6.68(d, J=2.56 Hz, 1H), 6.45(dd, J=2.20, 8.06 Hz, 1H), 6.38(br.s, 2H), 6.03(br.s, 2H), 5.62(t, J=6.96 Hz, 1H), 2.87(m, 1H), 2.72(m, 1H), 2.13 (m, 2H).

EXAMPLE 96

N-Hydroxy-N-{5-(4-fluorophenoxy)indan-1-yl}urea

STRUCTURE:

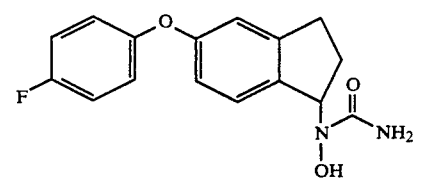

m.p.: 175.2°–176.6° C.

IR: ν (KBr): 3460, 3250, 2950, 1650, 1580, 1500, 1430, 1320, 1200 cm⁻¹.

NMR: δ (DMSO-d₆): 8.97(s, 1H), 7.18(m, 3H), 7.02(m, 2H), 6.79(m, 2H), 6.39(br.s, 2H), 5.63(t, J=7.32 Hz, 1H), 2.87(m, 1H), 2.72(m, 1H), 2.15(m, 2H).

EXAMPLE 97

N-Hydroxy-N-{5-(3-fluoro-4-methoxyphenoxy)indan-1-yl}urea

STRUCTURE:

-continued

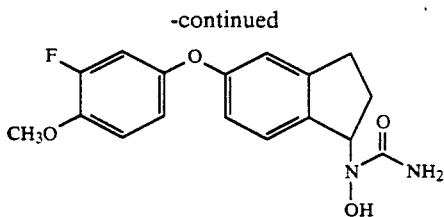

m.p.: 166.3°–167.5° C.

IR: ν (KBr): 3200–3500, 2950, 1660, 1510, 1490, 1440, 1260, 1150, 970 cm$^{-1}$.

NMR: δ (DMSO-d$_6$): 8.97(s, 1H), 7.14(m, 2H), 6.97(dd, J=2.57, 12.09 Hz, 1H), 6.79(m, 3H), 6.39(br.s, 2H), 5.62(t, J=7.33 Hz, 1H), 3.81(s, 3H), 2.86(m, 1H), 2.73(m, 1H), 2.14(m, 2H).

EXAMPLE 98

N-Hydroxy-N-{5-(3-trifluoromethylphenoxy)indan-1-yl}urea

STRUCTURE:

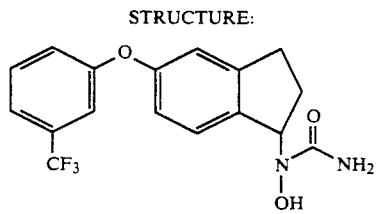

m.p.: 164.0°–165.1° C.

IR: ν (KBr): 3450, 3300, 2900, 1650, 1630, 1320, 800 cm$^{-1}$.

NMR: δ (DMSO-d$_6$): 9.00 (s, 1H), 7.60(t, J=7.70 Hz, 1H), 7.46(d, J=7.70 Hz, 1H), 7.23(m, 3H), 6.90(m, 2H), 6.42(s, 2H), 5.66(t, J=7.33 Hz, 1H), 2.89(m, 1H), 2.76(m, 1H), 2.18(m, 2H).

EXAMPLE 99

N-Hydroxy-N-{5-(3-methylphenoxy)indan-1-yl}urea

STRUCTURE:

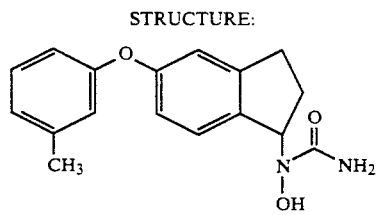

m.p.: 163.9°–165.4° C.

IR: ν (KBr): 3450, 3000–3400, 2850, 1660, 1570, 1480, 1260, 1150, 950 cm$^{-1}$.

NMR: δ (DMSO-d$_6$): 8.97(s, 1H), 7.24(t, J=7.70 Hz, 1H), 7.14(d, J=8.79 Hz, 1H), 6.93(d, J=7.32 Hz, 1H), 6.78(m, 4H), 6.40(br.s, 2H), 5.64(t, J=8.06 Hz, 1H), 2.88(m, 1H), 2.73(m, 1H), 2.28(s, 3H), 2.14(m, 2H).

EXAMPLE 100

N-Hydroxy-N-{5-(4-methoxyphenoxy)indan-1-yl}urea

STRUCTURE:

-continued

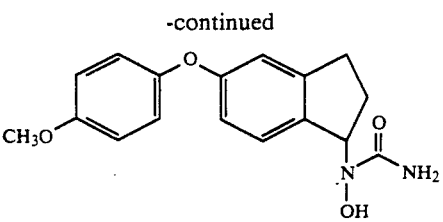

m.p.: 159.0°–160.2° C.

IR: ν (KBr): 3450, 3300, 2800–3000, 1670, 1650, 1580, 1500, 1240, 1030, 920, 910 cm$^{-1}$.

NMR: δ (DMSO-d$_6$): 8.94(s, 1H), 7.10(d, J=7.70 Hz, 1H), 6.95(m, 4H), 6.71(m, 2H), 6.38(br.s, 2H), 5.61(t, J=6.96 Hz, 1H), 3.74(s, 3H), 2.86(m, 1H), 2.71(m, 1H), 2.13(m, 2H).

EXAMPLE 101

N-Hydroxy-N-{5-(3-fluoro-4-methylphenoxy)indan-1-yl}urea

STRUCTURE:

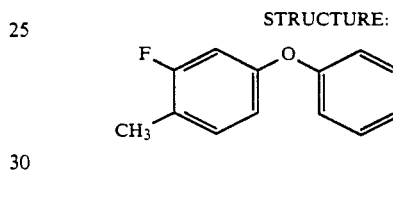

m.p.: 156.1°–157.5° C.

IR: ν (KBr): 3450, 3200, 2950, 1660, 1580, 1450, 1280, 1150, 1100, 960, 910 cm$^{-1}$.

NMR: δ (DMSO-d$_6$): 8.97(s, 1H), 7.26(t, J=8.79 Hz, 1H), 7.15(d, J=8.79 Hz, 1H), 6.77(m, 4H), 6.40(br.s, 2H), 5.64(t, J=6.96 Hz, 1H), 2.87(m, 1H), 2.74(m, 1H), 2.16(m, 2H).

EXAMPLE 102

N-Hydroxy-N-{5-(3,4-difluorophenoxy)indan-1-yl}urea

STRUCTURE:

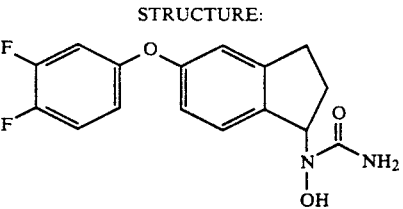

m.p.: 167.9°–169.1° C.

IR: ν (KBr): 3450, 3250, 1660, 1520, 1490, 1420, 1250, 1150, 960, 940 cm$^{-1}$.

NMR: δ (DMSO-d$_6$): 8.99(s, 1H), 7.43(m, 1H), 7.14(m, 2H), 6.83(m, 3H), 6.41(br.s, 2H), 5.64(t, 7.33 Hz, 1H), 2.88(m, 1H), 2.75(m, 1H), 2.16(m, 2H).

EXAMPLE 103

N-Hydroxy-N-(5-cinnamyloxyindan-1-yl)urea

STRUCTURE:

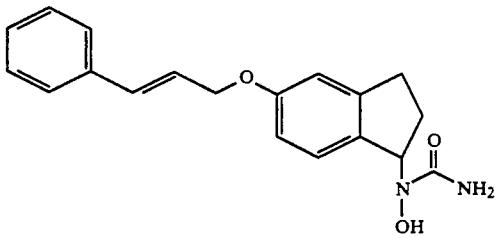

m.p.: 170.0°–171.3° C.

IR: ν (KBr): 3450, 3200, 2850, 1680, 1580, 1500, 1460, 1250, 1150, 970 cm$^{-1}$.

NMR: δ (DMSO-d$_6$): 8.90(bs, 1H), 7.50(m, 2H), 7.36(m, 3H), 7.06(d, J=8.43 Hz, 1H), 6.77(m, 3H), 6.65(m, 1H), 6.35(br.s, 2H), 5.59(t, J=6.59 Hz, 1H), 4.69(d, J=5.86 Hz, 1H), 2.89(m, 1H), 2.73(m, 1H), 2.14(m, 2H).

EXAMPLE 104

N-Hydroxy-N-{5-(5-trifluoromethyl-2-pyridyloxy)indan-1-yl}urea

STRUCTURE:

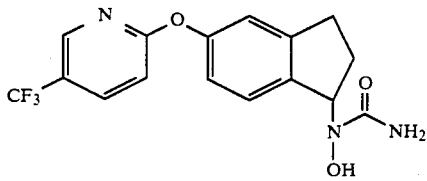

m.p.: 155.0°–156.3° C.

IR: ν (KBr): 3450, 3200, 2900, 1670, 1610, 1580, 1490, 1420, 1390, 1130, 1080, 940 cm$^{-1}$.

NMR: δ (DMSO-d$_6$): 9.05(s, 1H), 8.55(m, 1H), 8.20(d, J=2.56, 8.06 Hz, 1H), 7.20(d, J=8.43 Hz, 2H), 6.98(m, 2H), 6.43(br.s, 2H), 5.67(t, J=7.33 Hz, 1H), 2.90(m, 1H), 2.76(m, 1H), 2.14(m, 2H).

EXAMPLE 105

N-Hydroxy-N-{5-(3-chloro-2-pyridyloxy)indan-1-yl}urea

STRUCTURE:

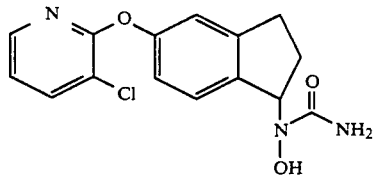

m.p.: 169.3°–170.4° C.

IR: ν (KBr): 3450, 3350, 2900, 1630, 1580, 1420, 1250, 1130, 1040, 940 cm$^{-1}$.

NMR: δ (DMSO-d$_6$): 9.50(s, 1H), 8.05(m, 2H), 7.16(m, 2H), 6.94(m, 2H), 6.42(br.s, 2H), 5.67(t, J=7.32 Hz, 1H), 2.89(m, 1H), 2.77(m, 1H), 2.17(m, 2H).

EXAMPLE 106

N-Hydroxy-N-{5-(4-chlorophenoxy)indan-1-yl}urea

STRUCTURE:

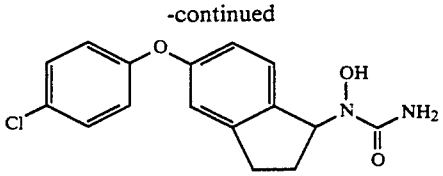

m.p.: 178.2°–179.0° C.

IR: ν (KBr): 3470, 3270, 1660, 1580, 1485, 1420, 1250 cm$^{-1}$.

NMR: δ (DMSO-d$_6$): 8.98 (s, 1H), 7.37–7.45 (m, 2H), 7.17 (d, J=7.7 Hz, 1H), 7.03–6.95 (m, 2H), 6.88–6.82 (m, 2H), 6.41 (s, 2H), 5.65 (t, J=7.5 Hz, 1H), 2.96–2.85 (m, 1H), 2.80–2.66 (m, 1H), 2.24–2.07 (m, 2H).

EXAMPLE 107

N-Hydroxy-N-{5-(2-pyridyloxy)indan-1-yl}urea

STRUCTURE:

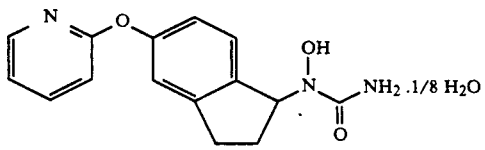

m.p.: 161.6°–162.8° C.

IR: ν (KBr): 3490, 3200, 1665, 1470, 1430 cm$^{-1}$.

NMR: δ (DMSO-d$_6$): 8.17 (s, 1H), 7.30–7.25 (m, 1H), 7.01–6.92 (m, 1H), 6.33–6.20 (m, 2H), 6.16–5.99 (m, 3H), 5.56 (s, 2H), 4.61 (t, J=7.5 Hz, 1H), 2.15–2.01 (m, 1H), 1.96–1.83 (m, 1H), 1.44–1.20 (m, 2H).

EXAMPLE 108

N-Hydroxy-N-{5-(4-methylphenoxy)indan-1-yl}urea

STRUCTURE:

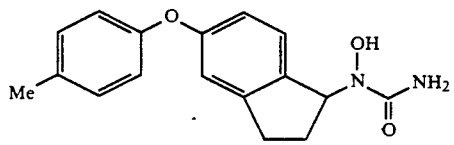

m.p.: 163.0°–163.7° C.

IR: ν (Nujol): 3460, 3190, 1665, 1575, 1224 cm$^{-1}$.

NMR: δ (DMSO-d$_6$): 8.98 (s, 1H), 7.18 (d, J=8.5 Hz, 2H), 7.13 (d, J=9.0 Hz, 1H), 6.89 (d, J=8.5 Hz, 2H), 6.77 (d, J=6.0 Hz, 2H), 6.40 (s, 2H), 5.63 (t, J=7.5 Hz, 1H), 2.94–2.83 (m, 1H), 2.77–2.65 (m, 1H), 2.28 (s, 3H), 2.23–2.05 (m, 2H).

EXAMPLE 109

N-Hydroxy-N-{5-(3-phenylpropyloxy)indan-1-yl}urea

STRUCTURE:

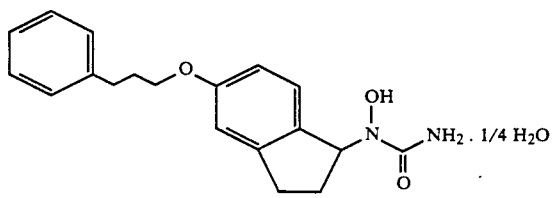

m.p.: 160.5°–162.0° C.

IR: ν (KBr): 3460, 3200, 1670, 1244, 1039 cm$^{-1}$.

NMR: δ (DMSO-d₆): 8.90 (s, 1H), 7.32-7.15 (m, 5H), 7.04 (d, J=8.0 Hz, 1H), 6.75-6.70 (m, 2H), 6.35 (s, 2H), 5.59 (t, J=7.5 Hz, 1H), 3.92 (t, J=6.5 Hz, 1H), 2.89-2.83 (m, 1H), 2.76-2.67 (m, 3H), 2.21-1.94 (m, 4H).

EXAMPLE 110

N-Hydroxy-N-{5-(2-thiazolyloxy)indan-1-yl}urea

STRUCTURE:

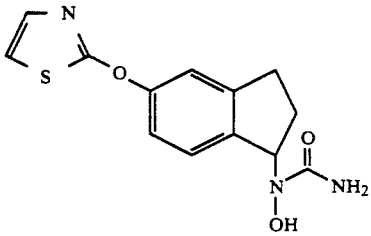

m.p.: 138.1°-139.9° C.

IR: ν (KBr): 3450, 3000-3400, 2950, 1670, 1570, 1440, 1240, 1160, 940 cm⁻¹.

NMR: δ (DMSO-d₆): 9.40(s, 1H), 7.27(d, J=3.66 Hz, 1H), 7.15(m, 4H), 6.44(br.s, 2H), 5.67(t, J=7.69 Hz, 1H), 2.91(m, 1H), 2.79(m, 1H), 2.18(m, 2H).

EXAMPLE 111

N-Hydroxy-N-{5-(4-tetrahydropyranyloxy)indan-1-yl}urea

STRUCTURE:

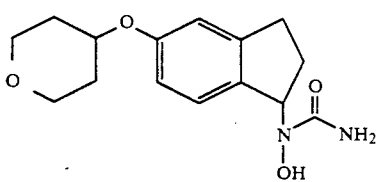

m.p.: 152.4°-153.9° C.

IR: ν (KBr): 3450, 3200, 2950, 2850, 1670, 1580, 1490, 1450, 1240, 1140, 1150, 1090, 1070, 990, 860, 810 cm⁻¹.

NMR: δ (DMSO-d₆): 8.89(s, 1H), 7.39(d, J=8.06 Hz, 1H), 6.80(br.s, 1H), 6.74(d, J=8.43 Hz, 1H), 6.35(br.s, 2H), 5.58(t, J=6.96 Hz, 1H), 4.50(m, 1H), 3.83(m, 2H), 3.43(m, 2H), 2.87(m, 1H), 2.70(m, 1H), 2.11(m, 2H), 1.94(m, 2H).

EXAMPLE 112

N-Hydroxy-N-{5-(6-methoxy-2-pyridyloxy)indan-1-yl}urea

STRUCTURE:

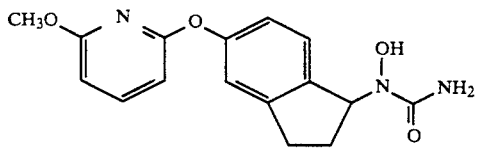

mp: 128.2°-128.7° C.

IR (Nujol) cm⁻¹: 3460, 3190, 1245, 1143, 1037.

NMR (DMSO-d₆) δ: 9.03 (s, 1H), 7.70 (t, J=8.0 Hz, 1H), 7.18 (d, J=8.0 Hz, 1H), 6.97 (s, 1H), 6.93 (dd, J=2.0 and 8.0 Hz, 1H) 6.52 (d, J=8.0 Hz, 1H), 6.42 (s, 2H), 6.37 (d, J=8.0 Hz, 1H), 5.67 (t, J=7.5 Hz, 1H), 3.71 (s, 3H), 2.98-2.87 (m, 1H), 2.81-2.70 (m, 1H), 2.27-2.08 (m, 2H).

EXAMPLE 113

N-Hydroxy-N-{5-(3,4-dimethoxyphenoxy)indan-1-yl}urea

STRUCTURE:

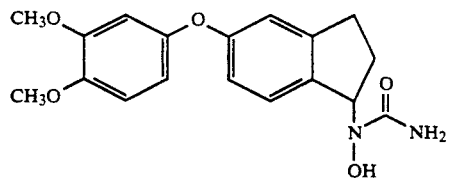

mo: 148.1°-149.3° C.

IR (KBr) cm⁻¹: 3450, 3200, 2850, 1670, 1580, 1520, 1470, 1450, 1230, 1150, 1110, 1020, 960.

NMR (DMSO-d₆) δ: 8.94(s, 1H), 7.11(d, J=8.06 Hz, 1H), 6.93(d, J=8.79 Hz, 1H) 6.74(m, 3H), 6.94(dd, J=2.92, 8.79 Hz, 1H), 6.38(br.s, 2H) 5.62(t, J=6.96 Hz, 1H), 3.73(s, 3H), 3.72(s, 3H), 2.84(m, 1H), 2.71(m, 1H), 2.14(m, 2H).

We claim:

1. A compound of the formula

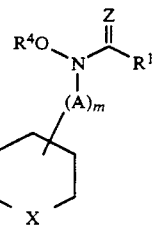

wherein $R^1$ is C1 to C4 alkyl or $-NR^2R^3$;

$R^2$ and $R^3$ are each independently hydrogen or C1 to C4 alkyl;

$R^4$ is hydrogen, a pharmaceutically acceptable cation, aroyl or C1 to C12 alkanoyl;

X is $NR^5$;

$R^5$ is hydrogen, C1 to C6 alkyl, C3 to C6 alkenyl, C1 to C6 alkanoyl, aryl, arylalkyl or aroyl;

m is 0 or 1;

n is 1;

A is C1 to C6 alkylene, C2 to C6 alkenylene or C2 to C6 alkylidene;

each Y is independently hydrogen, halogen, hydroxy, cyano, C1 to C12 alkyl, halosubstituted alkyl, hydroxysubstituted alkyl, C2 to C12 alkenyl, C1 to C12 alkoxy, C1 to C12 alkenyloxy, C1 to C8 cycloalkyl, C1 to C8 thioalkyl, C1 to C12 alkoxycarbonyl, C1 to C12 arylalkoxycarbonyl, aminocarbonyl, C1 to C12 alkylaminocarbonyl, C1 to C12 dialkylaminocarbonyl, C1 to C12 arylalkylamino, C1 to C12 arylalkylaminocarbonyl, alkoxyalkyl, aryl, aryloxy aroyl, C1 to C12 arylalkyl, C2 to C12 arylalkenyl, C1 to C12 arylalkoxy or C1 to C12 arylthioalkoxy wherein said aryl, aryloxy, aroyl, arylalkyl, arylalkenyl, arylalkoxy or arylthioalkoxy may be optionally substituted with a substituent or substituents selected from the group consisting of halo, nitro, cyano, C1 to C12 alkyl, halosubstituted alkyl and C1 to C12 alkoxy; and Z is oxygen or sulfur.

2. A compound according to claim 1 wherein $R^4$ is H.

3. A compound according to claim 2 wherein Z is O.

4. A compound according to claim 3 wherein R[1] is NH$_2$.

5. A compound according to claim 4 having the structure

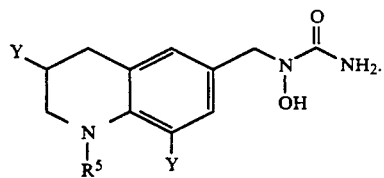

6. A compound according to claim 5 wherein R[5] is aryl or arylalkyl.

7. A compound according to claim 6 which is
N-hydroxy-N-[1-(3-methoxybenzyl)-1,2,3,4-tetrahydroquinolin-6-yl]methylurea;
N-hydroxy-N-[1-(3-trifluoromethylbenzyl)-1,2,3,4-tetrahydroquinolin-6-yl]methylurea;
N-hydroxy-N-[1-(3,5-dimethoxybenzyl)-1,2,3,4-tetrahydroquinolin-6-yl]methylurea;
N-hydroxy-N-[1-(3-allyloxybenzyl)-1,2,3,4-tetrahydroquinolin-6-yl]methylurea;
N-(1-phenyl-1,2,3,4-tetrahydroquinolin-6-yl)methyl-N-hydroxyurea;
N-hydroxy-N-(3-methoxy-1-phenyl-1,2,3,4-tetrahydroquinolin-6-yl)methylurea;
N-hydroxy-N-(3-allyloxy-1-phenyl-1,2,3,4-tetrahydroquinolin-6-yl)methylurea;
N-hydroxy-N-[1-(3-methoxybenzyl)-8-fluoro-1,2,3,4-tetrahydroquinolin-6-yl]methylurea;
N-hydroxy-N-[1-(3-difluoromethoxybenzyl)-1,2,3,4-tetrahydroquinolin-6-yl]methylurea; or
N-hydroxy-N-[1-(3-difluoromethoxybenzyl)-8-fluoro-1,2,3,4-tetrahydroquinolin-6-yl]methylurea.

8. A pharmaceutical composition comprising a pharmaceutically acceptable carrier and a lipoxygenase-inhibiting amount of a compound according to claim 1, 4, or 6.

9. A method of treating inflammatory conditions in a mammal comprising administering to said mammal an effective amount of a compound according to claim 6.

10. A method of inhibiting lipoxygenase activity in a mammal comprising administering to said mammal a lipoxygenase-inhibiting amount of a compound according to claim 6.

11. A method of inhibiting lipoxygenase activity in a mammal comprising administering to said mammal a pharmaceutical composition according to claim 8.

12. N-Hydroxy-N-[1-(3-phenylpropyl)-1,2,3,4-tetrahydroquinolin-6-yl]methylurea.

UNITED STATES PATENT AND TRADEMARK OFFICE
CERTIFICATE OF CORRECTION

PATENT NO. : 5,256,789

DATED : October 26, 1993

INVENTOR(S) : Rodney W. Stevens et al.

It is certified that error appears in the above-identified patent and that said Letters Patent is hereby corrected as shown below:

At column 1, line 45, replace "lipoxygenase" with --lipoxygenase inhibitors--;

At column 2, line 7, replace "hal6substituted" with --halosubstituted--;

At column 2, line 44, replace "brono" with --bromo--;

At column 2, line 52, replace "alkylazinocarbonyl" with --alkylaminocarbonyl--;

At column 2, line 53, replace "diaklylazinocarbonyl" with --dialkylaminocarbonyl--;

At column 4, line 59, replace "dinethylsulfide" with --dimethylsulfide--;

At column 7, line 1, replace "(3, 1H)" with --(m, 1H)--;

At column 8, line 56, replace "716" with --7.16--;

At column 11, line 41, replace "1633" with --1663--;

At column 16, line 32, replace "buten-2-acetamide" with --buten-2-yl]acetamide--;

At column 17, line 2, replace "695" with --6.95--;

UNITED STATES PATENT AND TRADEMARK OFFICE
CERTIFICATE OF CORRECTION

PATENT NO. : 5,256,789
DATED : October 26, 1993
INVENTOR(S) : Rodney W. Stevens et al It is certified that error appears in the above-indentified patent and that said Letters Patent is hereby corrected as shown below:

At column 17, line 4, replace "2.66" with --2.68--;

At column 23, line 15, replace "13.7" with --130.7--;

At column 23, line 21, insert --1.61-1.74 (m, 2H), 1.26-1.44 (m, 4H), 0.88 (t, J=7.3 Hz, 3H)-- after "2H)";

At column 27, line 6 replace "6.29" with --6.20--;

At column 36, line 6, replace "2.89" with --2.98--;

At column 38, line 17, replace "Hz, 6.43" with --Hz, 1H), 6.43--;

UNITED STATES PATENT AND TRADEMARK OFFICE
CERTIFICATE OF CORRECTION

PATENT NO. : 5,256,789
DATED : October 26, 1993
INVENTOR(S) : Rodney W. Stevens et al It is certified that error appears in the above-indentified patent and that said Letters Patent is hereby corrected as shown below:

At column 43, line 19, replace "Hz, 1H" with --Hz, 2H --;
At column 45, line 3, replace "6.5 Hz, 1H with --6.5 hz, 2H --;
At column 46, line 52, replace "C1 to C12" with --C3 to C12 --;
At column 46, line 52, replace "C1 to C8" with --C3 to C8 --;

Signed and Sealed this

Eighteenth Day of October, 1994

Attest:

BRUCE LEHMAN

Attesting Officer      Commissioner of Patents and Trademarks